(12) United States Patent
Alexanderson et al.

(10) Patent No.: US 10,439,611 B2
(45) Date of Patent: Oct. 8, 2019

(54) STERILE HANDLE CONTROL MECHANISM

(71) Applicant: Stryker Corporation, Kalamazoo, MI (US)

(72) Inventors: James K. Alexanderson, Coppell, TX (US); Wojciech K. Timoszyk, Flower Mound, TX (US); Vikas Kumar, Haryana (IN); Sudhanshu Mehta, Punjab (IN); Robert L. York, Lantana, TX (US)

(73) Assignee: Stryker Corporation, Kalamazoo, CA (US)

( * ) Notice: Subject to any disclaimer, the term of this patent is extended or adjusted under 35 U.S.C. 154(b) by 475 days.

(21) Appl. No.: 15/019,372

(22) Filed: Feb. 9, 2016

(65) Prior Publication Data

US 2016/0230974 A1     Aug. 11, 2016

Related U.S. Application Data

(60) Provisional application No. 62/114,757, filed on Feb. 11, 2015.

(51) Int. Cl.
*H03K 17/965* (2006.01)
*H01H 19/14* (2006.01)
(Continued)

(52) U.S. Cl.
CPC ........... *H03K 17/965* (2013.01); *A61B 90/30* (2016.02); *H01H 19/04* (2013.01); *H01H 19/08* (2013.01); *H01H 19/14* (2013.01); *H03K 17/945* (2013.01); *A61B 2034/2048* (2016.02); *A61B 2090/308* (2016.02); *A61B 2090/309* (2016.02); *F21W 2131/205* (2013.01); *F21Y 2115/10* (2016.08); *H01H 2221/01* (2013.01); *H01H 2231/052* (2013.01); *H03K 2017/9455* (2013.01)

(58) Field of Classification Search
CPC ....... A61B 90/30; A61B 46/10; Y10S 16/906; F21V 21/403
See application file for complete search history.

(56) References Cited

U.S. PATENT DOCUMENTS 5,604,955 A    2/1997 Horan
5,788,688 A    8/1998 Bauer et al.
(Continued)

FOREIGN PATENT DOCUMENTS

GB    2 423 378 A    8/2006

OTHER PUBLICATIONS

Extended European Search Report with Written Opinion issued in Appln. No. 16155273.2 dated Jun. 20, 2016 (10 pages).
(Continued)

*Primary Examiner* — Andrew Yang
(74) *Attorney, Agent, or Firm* — Morrison & Foerster LLP

(57) ABSTRACT

A surgical light including a light housing having at least one light source therein and a handle assembly extending from the light housing, with the handle assembly including a knob and a cover. The handle assembly is rotatably connected to the light housing. The cover covers the knob. Engaging the cover in a first mode and rotating the knob alters a first characteristic of light emitted from the at least one light source. Engaging the cover in a second mode and rotating the knob alters a second characteristic of light emitted from the at least one light source.

36 Claims, 17 Drawing Sheets

(51) Int. Cl.
    *H01H 19/08*     (2006.01)
    *H01H 19/04*     (2006.01)
    *H03K 17/945*     (2006.01)
    *A61B 90/30*     (2016.01)
    *F21W 131/205*     (2006.01)
    *F21Y 115/10*     (2016.01)
    *A61B 34/20*     (2016.01)

(56) References Cited

U.S. PATENT DOCUMENTS

| | | |
|---|---|---|
| 6,402,351 B1 | 6/2002 | Borders et al. |
| 6,644,837 B2 | 11/2003 | Borders et al. |
| 6,692,141 B2 | 2/2004 | Jesurun et al. |
| 6,863,422 B2 | 3/2005 | Jesurun et al. |
| 8,172,751 B2 | 5/2012 | Kusner et al. |
| 8,317,361 B2 | 11/2012 | Lee |
| 8,662,719 B2 | 3/2014 | Rohwedder et al. |
| 2002/0089857 A1 | 7/2002 | Borders et al. |
| 2003/0161158 A1 | 8/2003 | Jesurun et al. |
| 2003/0210559 A1 | 11/2003 | Jesurun et al. |
| 2010/0053085 A1 | 3/2010 | Hall |
| 2010/0053982 A1* | 3/2010 | Klaus .................. F21V 21/403 |
| | | 362/386 |
| 2014/0268751 A1 | 9/2014 | Boccoleri et al. |
| 2017/0056120 A1* | 3/2017 | Benatav ................ A61B 50/00 |

OTHER PUBLICATIONS

European Office Action dated on Oct. 12, 2018 for EP Application No. 16155273.2 filed Feb. 11, 2016, 4 pages.

* cited by examiner

STERILE HANDLE CONTROL MECHANISM

CROSS REFERENCE TO RELATED APPLICATION

This claims the benefit of U.S. Provisional Application Ser. No. 62/114,757, filed Feb. 11, 2015, which is incorporated herein by reference in its entirety.

FIELD OF THE INVENTION

The present invention relates to a surgical light, and in particular to a sterile control for a surgical light.

BACKGROUND OF THE INVENTION

Surgical lights have been used in operating rooms to provide increased light to a specific area of the room. For example, the surgical light can be positioned within an operating room and can provide increased light to a specific area of a person being operated on within the operating room. In the past, surgical lights have had one or more controls for adjusting aspects of the lights. For example, prior art surgical lights have included a rotating handle for adjusting a beam pattern of the light and a button for controlling an intensity of the light.

SUMMARY OF THE INVENTION

The present invention, according to one aspect, is directed to a surgical light comprising a light housing having at least one light source therein and a handle assembly extending from the light housing, with the handle assembly including a base, a knob and a cover. The base has at least one first sensor at a face of the base. The knob extends from the face of the base and is connected to the base. The cover covers the knob and the face of the base. The cover includes at least one first area for covering the at least one first sensor. The knob and the cover are movably mounted relative to the light housing. Movement of the knob and the cover without engagement of the first sensor by placing a digit of a user at the at least one first area causes alteration of a first characteristic of light emitted from the at least one light source. Movement of the knob and the cover with engagement of the first sensor by placing the digit of the user at the at least one first area causes alteration of a second characteristic of light emitted from the at least one light source.

Another aspect of the present invention includes providing a handle assembly comprising a base having at least one first sensor at a face of the base. The knob extends from the face of the base and is connected to the base. The cover covers the knob and the face of the base. The cover includes at least one first area for covering the at least one first sensor. Movement of the knob and the cover without engagement of the first sensor by placing a digit of a user at the at least one first area causes the base to send a first signal. Movement of the knob and the cover with engagement of the first sensor by placing the digit of the user at the at least one first area causes the base to send a second signal.

Yet another aspect of the present invention is to provide a surgical light handle cover and a face plate covering portion. The surgical light handle cover includes a knob covering portion having a circular side wall and a top wall. The face plate covering portion is connected to a bottom edge of the knob covering portion. The face plate covering portion includes a disc-shaped plate having a top surface and a bottom surface and a plurality of recessed portions extending from the bottom surface of the disc-shaped plate in a direction away from the knob covering portion.

Another aspect of the present invention is to provide a surgical light including a light housing having at least one light source therein and a handle assembly extending from the light housing. The handle assembly includes a knob and a cover. The knob and the cover are movably mounted relative to the light housing. The cover covers the knob. The handle assembly includes an actuator. A first activation of the actuator causes alteration of a first characteristic of light emitted from the at least one light source when the knob is rotated relative to the light housing. A second activation of the actuator causes alteration of a second characteristic of light emitted from the at least one light source when the knob is rotated relative to the light housing.

Yet another aspect of the present invention is to provide a method of adjusting attributes of light emitted from a surgical light including providing a light housing having at least one light source therein, providing a handle assembly extending from the light housing, with the handle assembly including a knob and a cover, rotatably connecting the handle assembly to the light housing, covering the knob with the cover, engaging the cover in a first mode and rotating the knob to thereby alter a first characteristic of light emitted from the at least one light source, and engaging the cover in a second mode and rotating the knob to thereby alter a second characteristic of light emitted from the at least one light source.

Another aspect of the present invention is to provide a surgical light including a light housing having at least one light source therein and a handle assembly extending from the light housing, with the handle assembly including a knob and a cover. The handle assembly is rotatably connected to the light housing. The cover covers the knob. Engaging the cover in a first mode and rotating the knob alters a first characteristic of light emitted from the at least one light source. Engaging the cover in a second mode and rotating the knob alters a second characteristic of light emitted from the at least one light source.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings and described in the following specification are simply exemplary embodiments of the inventive concepts. Hence, specific dimensions and other physical characteristics relating to the embodiments disclosed herein are not to be considered as limiting.

DETAILED DESCRIPTION

The reference number 10 (FIG. 1) generally designates a surgical light. The surgical light 10 is configured to be positioned within a room (e.g., operating room) and to provide increased light to a specific area of the room. While the surgical light 10 can be placed within an operating room, the surgical light 10 can also be placed in any area wherein increased light at a targeted location is desired. The surgical light 10 includes a light assembly 12 and an arm 14 for connecting the light assembly 12 to a static or movable structure within the operating room. For example, the arm 14 can be directly connected to a suspension system connected to a wall or ceiling of the operating room, can be connected to a further arm assembly (not shown) or suspension system directly connected to a wall or ceiling of the operating room, or can be directly or indirectly connected to a movable assembly located within the operating room.

Figure 1:
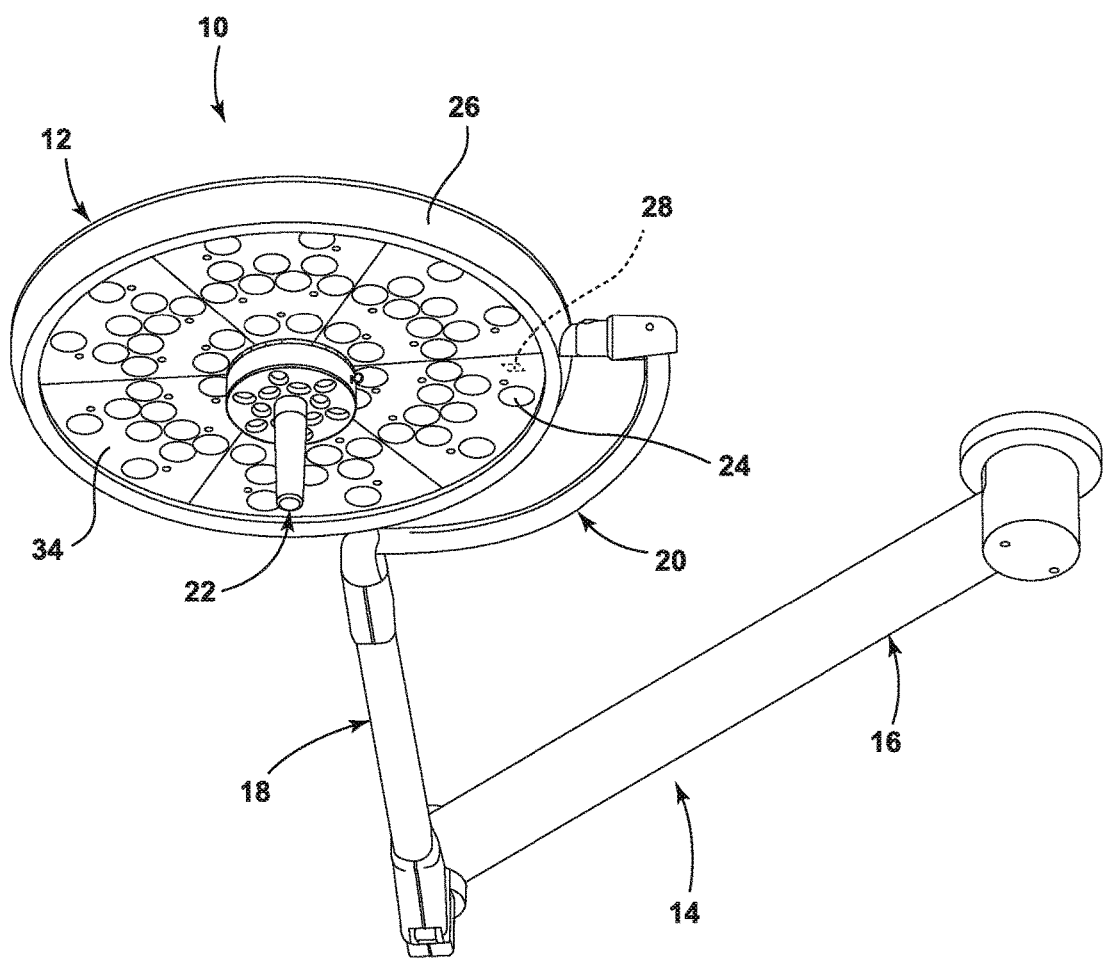
FIG. 1 illustrates a perspective view of a surgical light according to the invention.

In the illustrated example, the arm 14 of the surgical light 10 allows light from the light assembly 12 to be pointed at a certain area within the operating room (with the suspension system allowing the light assembly 12 to be selectively positioned within the operating room). The arm 14 includes a first arm member 16 configured to be rotatably connected to a support (e.g., a ceiling), a second arm member 18 rotatably connected to the first arm member 16, and a curved link 20 extending between the second arm member 18 and the light assembly 12. The first arm member 16, the second arm member 18 and the curved link 20 allow the light assembly 12 to be moved to any desired location by grasping a handle assembly 22 extending from a face of the light assembly 12 and pulling, pushing and/or twisting the light assembly 12 to any desired location. While a specific arm 14 is illustrated in FIG. 1, any arm well known to those skilled in the art could be used to connect the light assembly 12 to the operating room structure or a movable assembly as discussed above (including one connected to multiple points on the side of the light assembly 12 and/or the rear surface thereof). The illustrated arm 14 or any arm known to those skilled in the art allows for easy movement of the light assembly 12 into any position within the operating room and then maintaining the position of the light assembly 12 once released.

The illustrated light assembly 12 provides increased light to a targeted area of an operating room. The light assembly 12 includes a housing 26 having at least one light source 28 (e.g., LED) therein. Each light source 28 is covered by light directing optics 24. The housing 26 includes a circular face glass 34 covering the at least one light source 28, with the handle assembly 22 for moving the housing 26 extending from an opening in the center of the circular face glass 34. The handle assembly 22 is used for moving the light assembly 12 along with being capable of turning on, turning off, increasing and decreasing the intensity of the light emitted by the light source 28 within the light assembly 12 as discussed in more detail below. The handle assembly 22 can also control other features of the light emitted by the light source 28 within the light assembly 12 as discussed in more detail below. Housings for light assemblies and the light sources and optics therein are well known to those skilled in the art. For example, the housing, light source and optics can be those of U.S. Patent Application Publication No. 2014/0268751 entitled SURGICAL LIGHT WITH BEAM REDIRECTING OPTICS, the entire contents of which are incorporated herein by reference.

The illustrated handle assembly 22 (FIGS. 2 and 3) of an embodiment the invention is used to alter characteristics of the light assembly 12. The handle assembly 22 includes a base 40 having a substantially cylindrical knob 42 (see FIGS. 3 and 4) extending therefrom. The handle assembly 22 also includes a cover 44 covering the cylindrical knob 42 and the face 46 of the base 40. The handle assembly 22 is configured to move (e.g., rotate) to alter characteristics of the light assembly 12.

Figure 3:
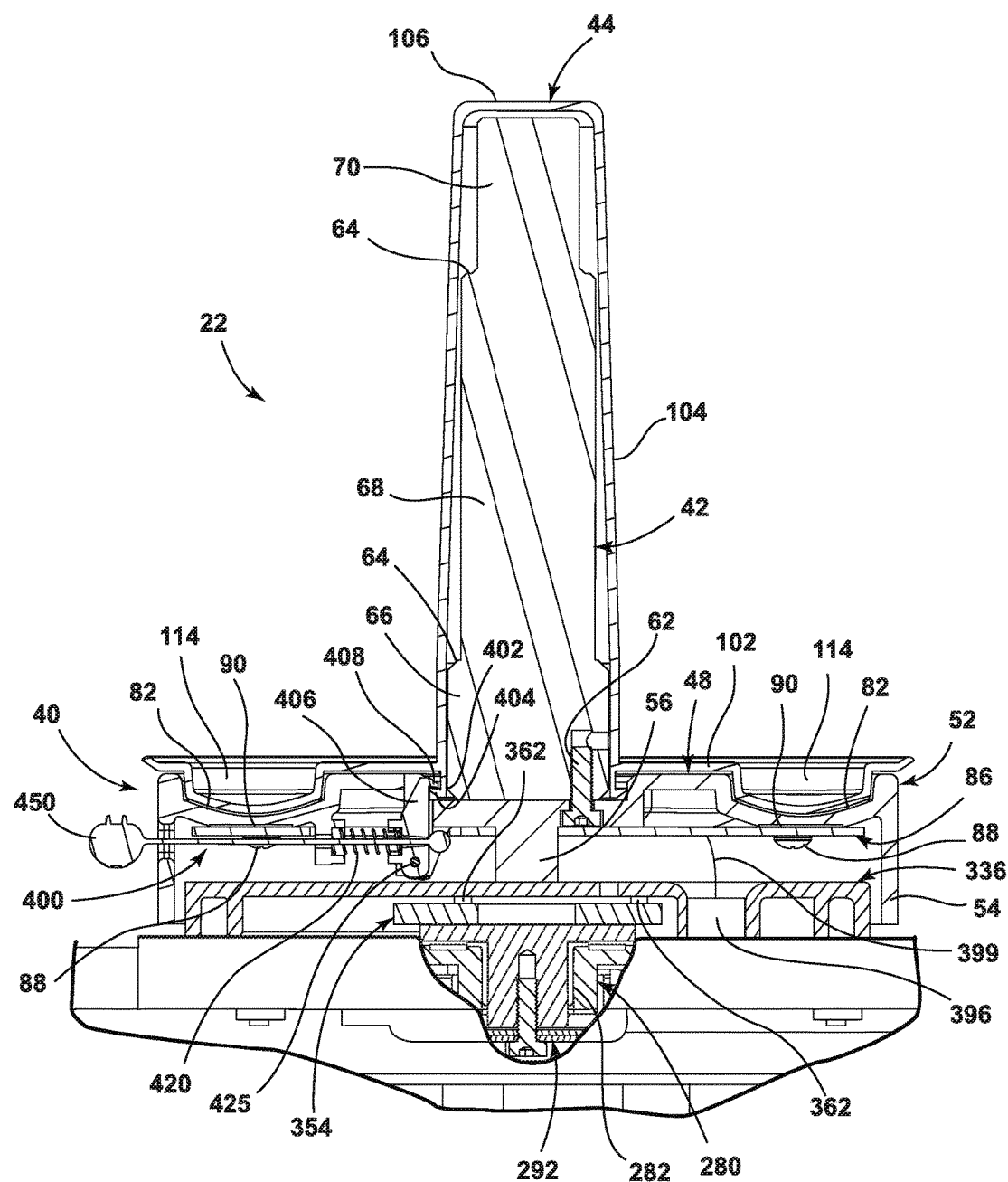
FIG. 3 is a partial cross-sectional view of the handle assembly according to the invention.

In the illustrated example, the base 40 extends from an opening in the center of the circular face glass 34 of the housing 26 of the light assembly 12. The base 40 includes a rotating platform 52 rotatable about a center of the circular face glass 34 of the housing 26. The rotating platform 52 includes a face plate 48 having the face 46 and has a cylindrical skirt 54 extending from a periphery of the face plate 46 toward the circular face glass 34 of the housing 26. As illustrated in FIG. 3, a pivot post 56 extends from a bottom surface of the face plate 48 and is connected to a disc 336. The disc 336 connects to a connection assembly 354 by a plurality of fasteners 362. The connection assembly 354 extends through a central opening 282 in a base disc 280 connected to the housing 26. The connection assembly 354 is connected to a switch plate 292 at a bottom end thereof. The disc 336, the connection assembly 354, the plurality of fasteners 362, the central opening 282, the base disc 280 and the switch plate 292 and their functions are well known to those skilled in the art. For example, U.S. Patent Application Publication No. 2014/0268751 described above discloses the disc 336, the connection assembly 354, the plurality of fasteners 362, the central opening 282, the base disc 280 and the switch plate 292 and how rotation of the pivot post 56 causes the switch plate 292 to rotate to actuate a first switch (e.g., optical, mechanical or electrical) during rotation of the pivot post 56 in a first direction and a second switch (e.g., optical, mechanical or electrical) during rotation of the pivot post 56 in a second direction opposite to the first direction. However, it is contemplated that any conventional system could be used for transferring rotation of the rotating platform 52 through an opening in the housing 26 to a device that actuates a first switch during rotation in a first direction and a second switch during rotation in a second direction opposite to the first direction.

Figure 4:
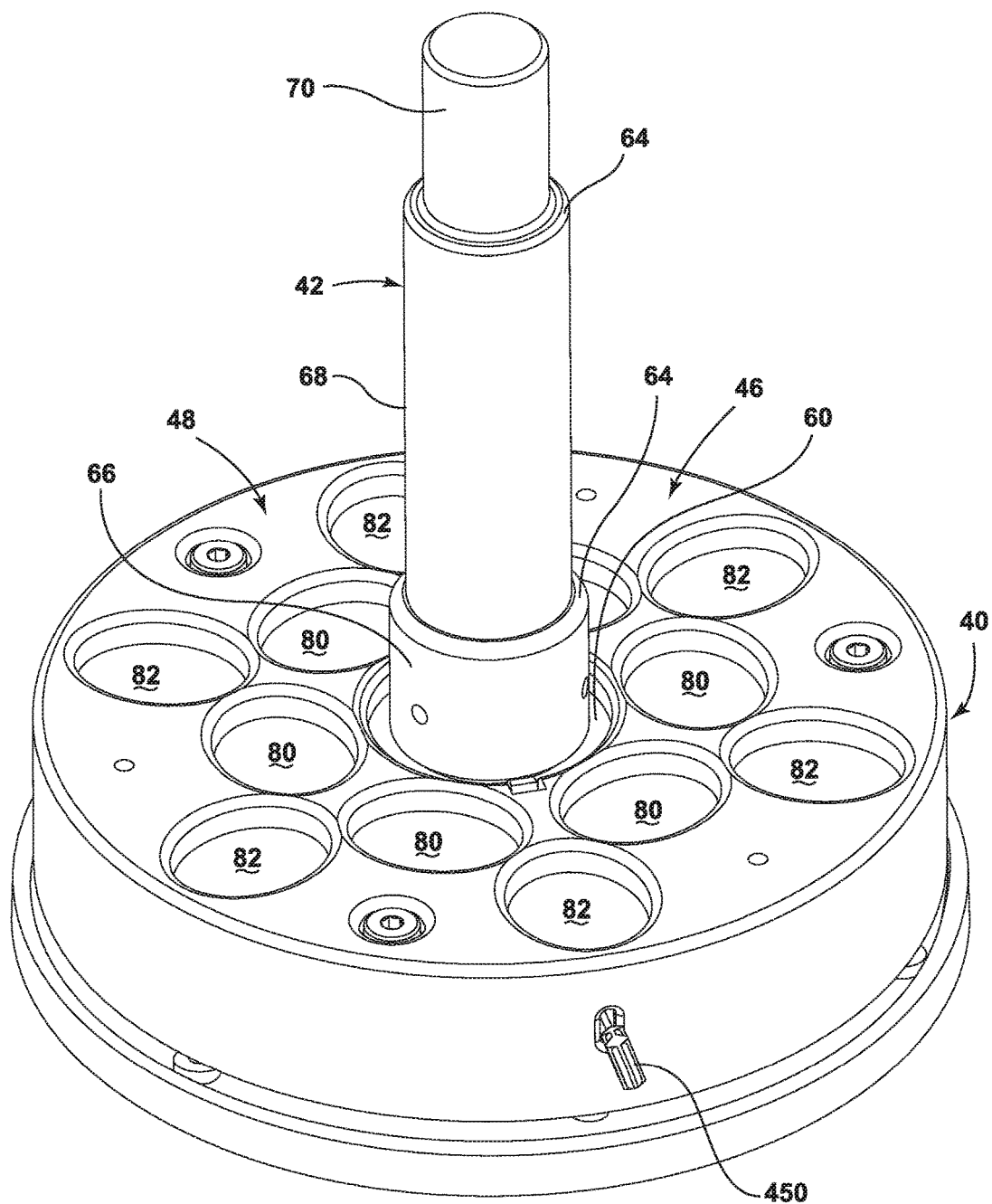
FIG. 4 is a front perspective view of a base and a knob of the handle assembly according to the invention with the cover removed.
Figure 5:
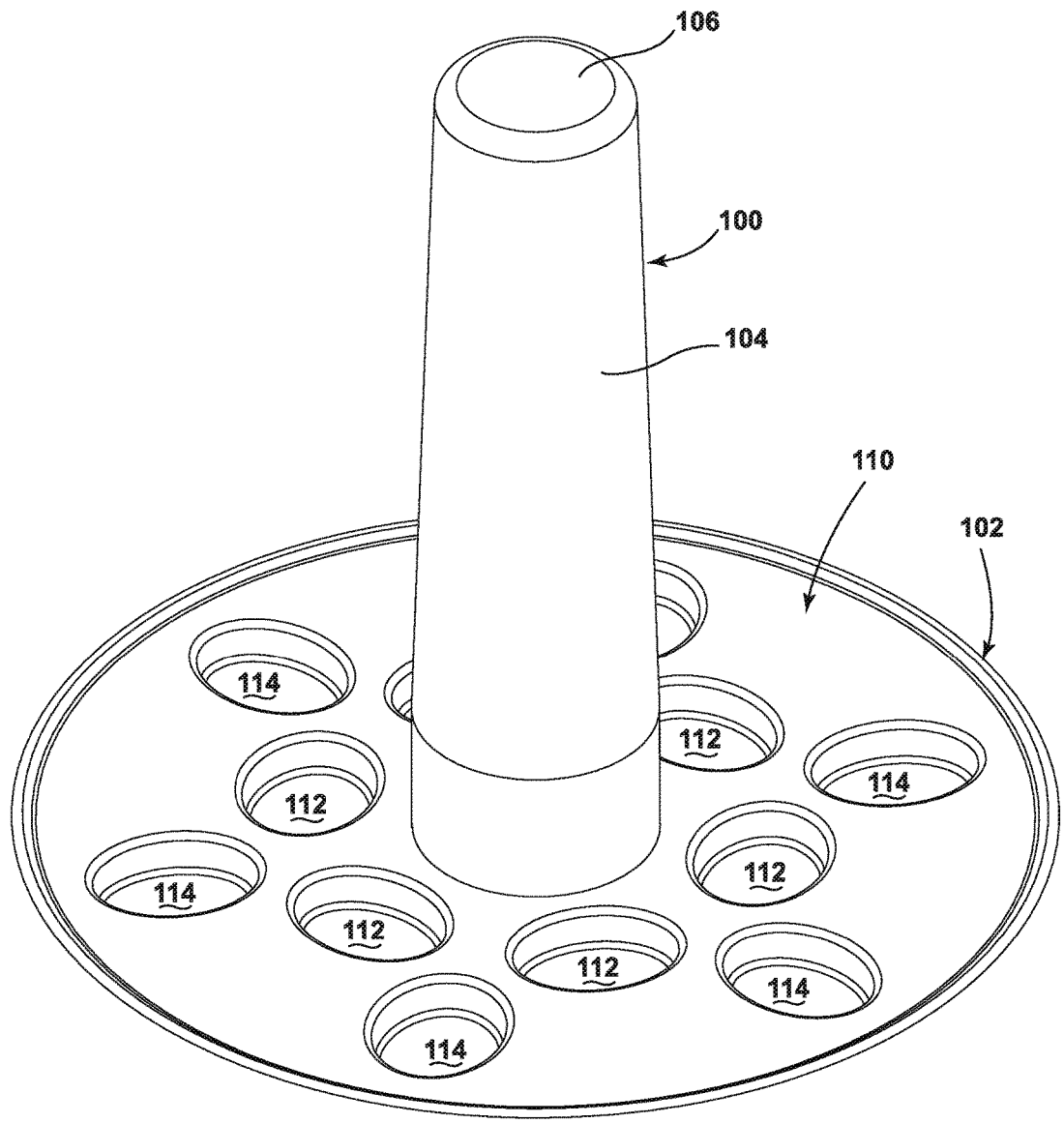
FIG. 5 is a front perspective view of a cover of the handle assembly according to the invention.

The illustrated knob 42 is connected to the face plate 48 and extends therefrom. As illustrated in FIG. 4, the face plate 48 includes a centrally located circular recess 60. The knob 42 is located in the centrally located circular recess 60 of the face plate 48. As illustrated in FIG. 5, a fastener 62 extends through the face plate 48 and into the knob 42 to fix the knob 42 to the face plate 48. In the illustrated example, the knob 42 includes a plurality of steps 64 dividing the knob 42 into a lower large circumference cylinder 66 having the fastener 62 inserted therein, a central middle circumference cylinder 68 and an upper small circumference cylinder 70. However, it is contemplated that the knob 42 could be a smooth surfaced cylinder having a straight outer surface or a slightly tapering outer surface. Moreover, it is contemplated that any or all of the lower large circumference cylinder 66, the central middle circumference cylinder 68 and the upper small circumference cylinder 70 could have a straight outer surface or a slightly tapering outer surface. As the knob 42 is grasped and rotated (typically through the cover 44), the face plate 48 will also rotate to thereby actuate a switch as outlined above.

In the illustrated example, the base 40 includes a plurality of controls for altering a characteristic of the surgical light 10 from movement (e.g., rotation) of the knob 42. As illustrated in FIG. 4, the controls are in the face plate 48 and include a plurality of inner recesses 80 forming a first inner circle about the centrally located circular recess 60 in the face plate 48. The face plate 48 also includes a plurality of outer recesses 82 forming a second outer circle about the inner circle of inner recesses 80 in the face plate 48. The inner recesses 80 and the outer recesses 82 are the controls for altering a characteristic of the surgical light 10 during movement (e.g., rotation) of the knob 42. In the illustrated example, there are six inner recesses 80 and five outer recesses 82. However, it is contemplated that any number of inner recesses 80 and/or outer recesses 82 could be used. Furthermore, it is contemplated that only one circle of recesses could be used or that more than two circles of recesses could be used. Moreover, it is contemplated that the inner recesses 80 and the outer recesses 82 could have different shapes and/or the same shape in different orientations to provide a tactile difference in the different recesses. For example, as shown in the illustrated embodiment, the inner recesses 80 are oval with the longer axis thereof being aligned in a circumferential direction and the outer recesses 82 are oval with the longer axis thereof being aligned in a radial direction.

As illustrated in FIG. 3, a circuit board 86 is connected to a rear surface of the face plate 48 by a plurality of fasteners 88. The circuit board 86 is configured to sense insertion of a digit (finger or thumb) of a user of the handle assembly 22 into at least one of the inner recesses 80 and/or outer recesses 82 in the face plate 48 of the base 40. The circuit board 86 can include a proximity sensor 90 located under each of the inner recesses 80 and outer recesses 82. The proximity sensor 90 can therefore sense when a digit is in an associated one of the inner recesses 80 and outer recesses 82. The proximity sensors 90 are configured to sense presence of the digit within the inner recesses 80 and/or the outer recesses 82, but not sense presence of the digit just above the inner recesses 80 and/or the outer recesses 82. It is contemplated that the depth of the inner recesses 80 and the outer recesses 82 can be about 0.315 inches with the proximity sensors 90 having a range through the cover 44 that is approximately 0.315 inches (the depth of the recesses). However, it is contemplated that other depths of the inner recesses 80 and/or the outer recesses 82 along with a corresponding range of the proximity sensors 90 to equal the depths of the inner recesses 80 and the outer recesses 82. Alternatively, the proximity sensor 90 can be replaced with a button or similar mechanical depression switch that can be activated by depression of at least one of the inner recesses 80 and outer recesses 82. If a proximity sensor 90 is used, the face plate 48 can be substantially rigid. However, if a button or similar mechanical switch is used, the face plate 48 should be deformable enough to allow depression of the button or similar depression switch.

In the illustrated example, the handle assembly 22 is employed to move the light assembly 12. In order to maintain a sterile environment between different surgical procedures, the cover 44 can be removed from the handle assembly 22 to be cleaned and/or replaced with another cover 44 after a surgical procedure to maintain a sterile environment. In the illustrated example, the cover 44 covers the face plate 48 and the knob 42 of the handle assembly 22. The cover 44 (FIG. 5) includes a knob covering portion 100 and a face plate covering portion 102. The knob covering portion 100 includes an outer frustoconical shell 104 having a slight taper and an end cap 106 at an end of the outer frustoconical shell 104. The face plate covering portion 102 includes a disc-shaped plate 110 extending radially from an end of the outer frustoconical shell 104 opposite the end cap 106. The disc-shaped plate 110 includes a plurality of recessed portions corresponding to the recesses 80 and 82 in the face plate 48. In the illustrated example, the recessed portions in the disc-shaped plate 110 include a plurality of inner recessed portions 112 forming a first inner circle about the outer frustoconical shell 104 and a plurality of outer recessed portions 114 forming a second outer circle about the inner circle of inner recessed portions 112 in the disc-shaped plate 110. The inner recessed portions 112 have an outer shape substantially conforming to the shape of the inner recesses 80 in the face plate 48 to allow the inner recessed portions 112 to be snugly received within the inner recesses 80. Likewise, the outer recessed portions 114 have an outer shape substantially conforming to the shape of the outer recesses 82 in the face plate 48 to allow the outer recessed portions 114 to be snugly received within the outer recesses 82 in the face plate 48. If the circuit board 86 includes proximity sensors 90, the cover 44 can be made of substantially rigid material or partially flexible material. However, if the circuit board 86 includes a button or similar depression switch, the cover 44 should be deformable enough to allow depression of the button or similar depression switch through the inner recesses 80 and outer recesses 82 in the face plate 48.

Figure 2:
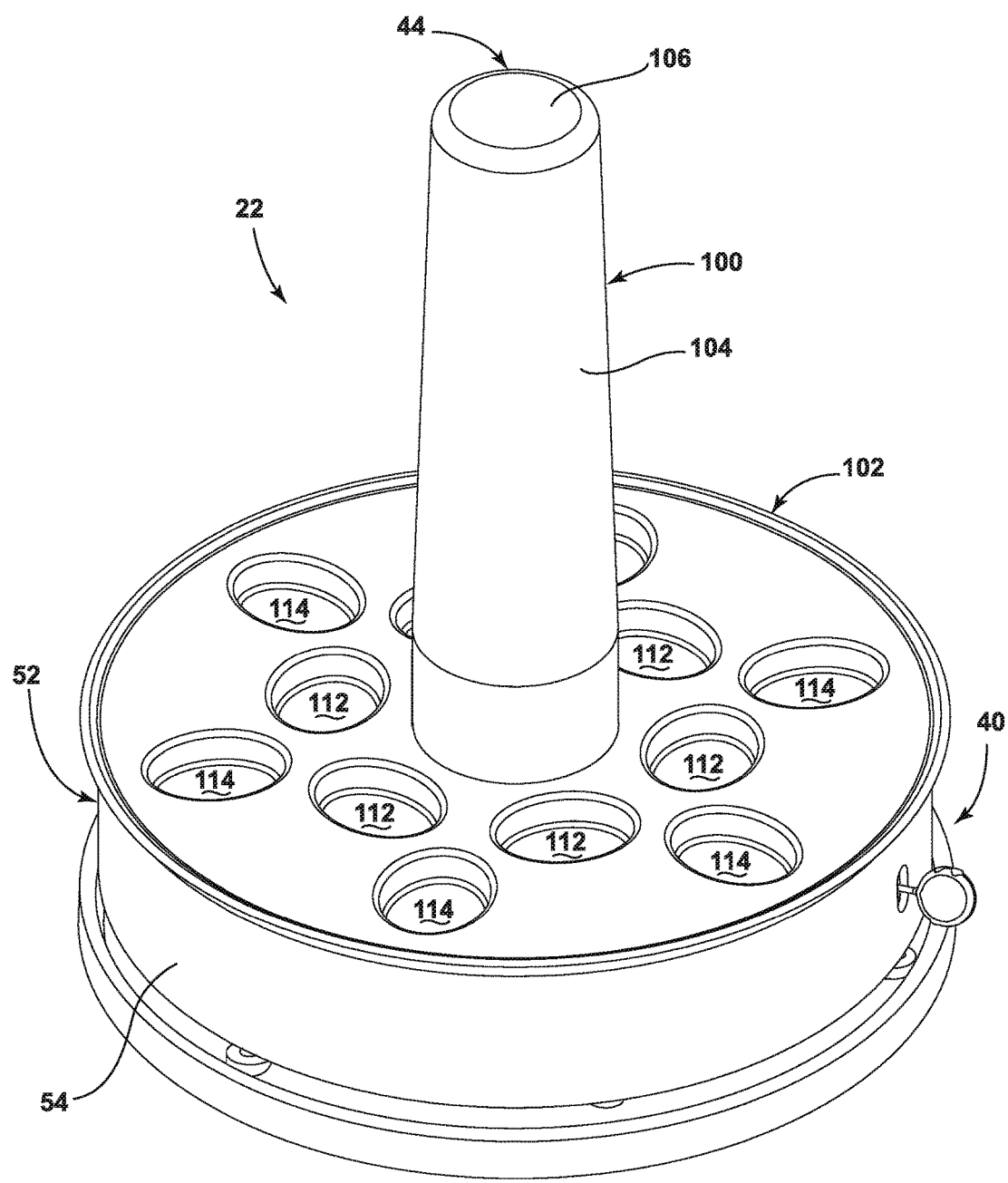
FIG. 2 is a front perspective view of a handle assembly of the surgical light according to the invention.
Figure 6:
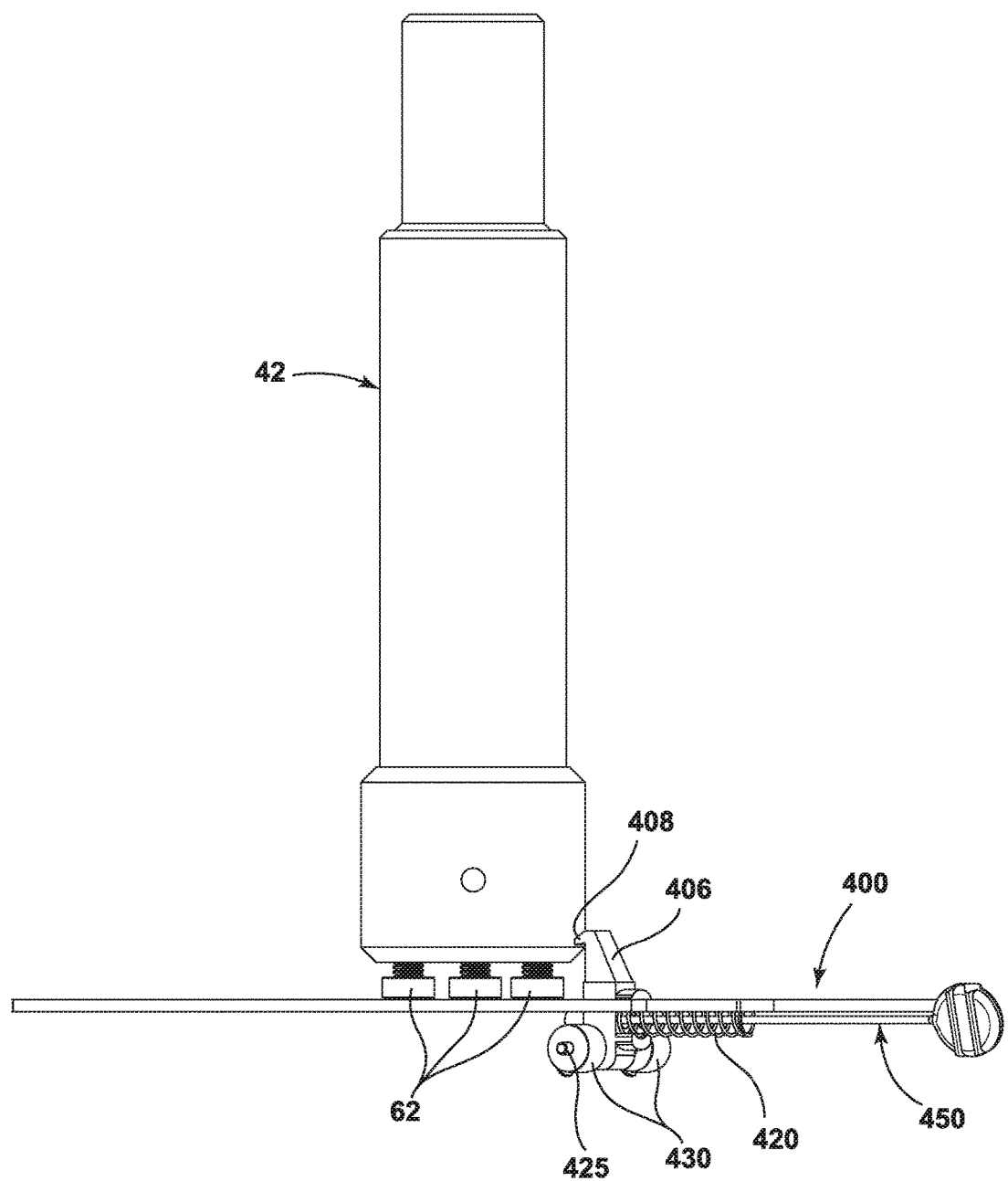
FIG. 6 is a side view of the knob of the handle assembly according to the invention illustrating a cover release system.

The illustrated cover 44 is configured to be locked to the base 40 by a locking mechanism 400 as shown in FIGS. 2, 3 and 6. In order to allow the cover 44 to be locked to the base 40, the cover 44 includes a cylinder 402 extending from a bottom surface of the face plate 48 in a direction away from the outer frustoconical shell 104. The cylinder 402 includes an outwardly radially extending locking lip 404 at an end of the cylinder 402 opposite the face plate 48. The locking mechanism 400 includes a locking lever 406 having a lock hook 408 at a top end thereof that hooks over the outwardly radially extending locking lip 404 of the cover 44 to lock the cover 44 in position over the face plate 48 and the knob 42. As illustrated in FIGS. 3 and 6, the locking lever 406 is biased towards the outwardly radially extending locking lip 404 of the cover 44 by a spring 420. A bottom of the locking lever 406 is pivotally connected to the face plate 48 by a pivot pin 425 that extends through the bottom of the locking lever 406 and a pair of posts 430 connected to the face plate 48. A pull pin 450 is connected to the locking lever 406 between the pivot pin 425 and the lock hook 408. The pull pin 450 can be pulled to rotate the locking lever 406 against the bias of the spring 420 to disengage the lock hook 408 from the outwardly radially extending locking lip 404 of the cover 44 to allow the cover 44 to be removed from the base 40. As illustrated in FIGS. 3 and 4, the pull pin 450 extends through an opening in the skirt 54 for easily removing the cover 44.

Figure 7:
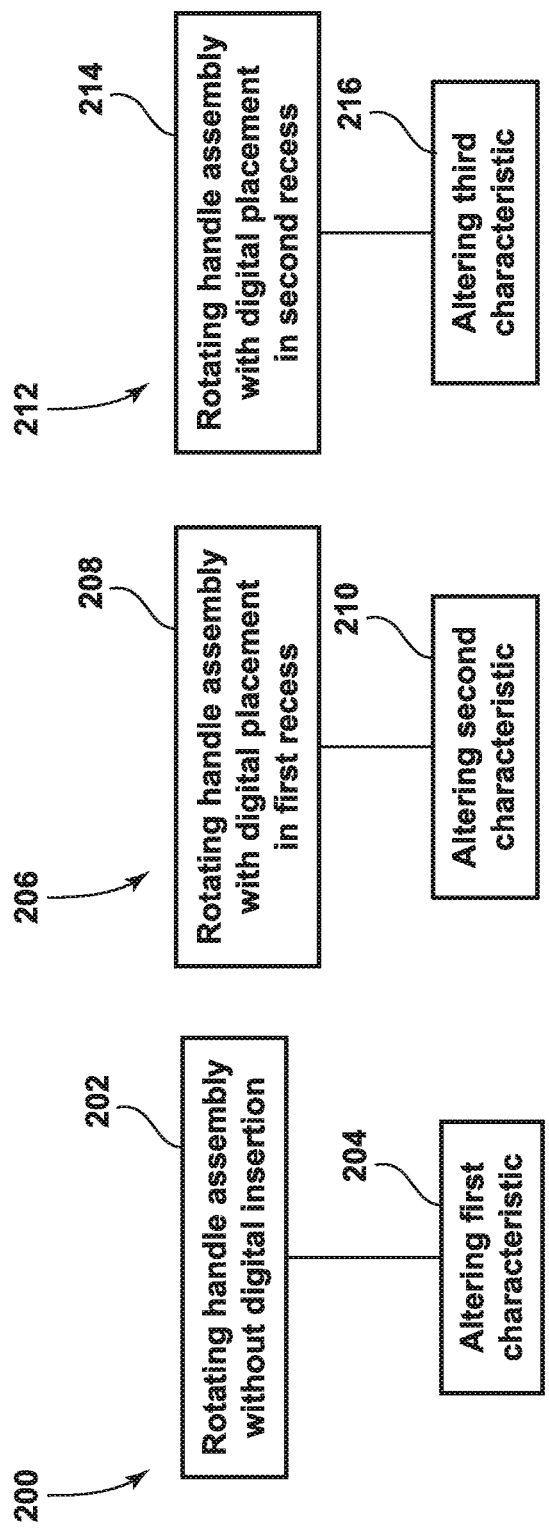
FIG. 7 illustrates a method of altering characteristics of the surgical light according to the invention.

In the illustrated embodiment, the handle assembly 22 is actuated to alter characteristics of the light assembly 12 (see FIG. 7). A first actuation method 200 includes moving (e.g., rotating) the handle assembly 22 (by grasping the knob 42 and the cover 44) without placing a digit within any of the inner recessed portions 112 and inner recesses 80 or the outer recessed portions 114 and the outer recesses 82 at step 202. Once the handle assembly 22 is moved (e.g., rotated) at step 202, a first characteristic of the light assembly 12 is altered at step 204. A second actuation method 206 includes moving (e.g., rotating) the handle assembly 22 (by grasping the knob 42 and the cover 44) and placing a digit within any of the inner recessed portions 112 and inner recesses 80, but not any of the outer recessed portions 114 and the outer recesses 82 at step 208. Once the handle assembly 22 is moved (e.g., rotated) at step 208, a second characteristic of the light assembly 12 is altered at step 210. A third actuation method 212 includes moving (e.g., rotating) the handle assembly 22 (by grasping the knob 42 and the cover 44) and placing a digit within any of the outer recessed portions 114 and the outer recesses 82, but not any of the inner recessed portions 112 and inner recesses 80 at step 214. Once the handle assembly 22 is moved (e.g., rotated) at step 214, a third characteristic of the light assembly 12 is altered at step 216.

As the illustrated handle assembly 22 is moved (e.g., rotated), characteristics of the light assembly 12 are altered. One characteristic of the light assembly 12 that can be altered is an intensity of the light emitted from the at least one light source 28. For example, movement (e.g., rotation) of the handle assembly 22 can increase or decrease the intensity of the light emitted by the at least one light source 28, turn the light source 28 on or turn the light source 28 off. More specifically, moving (e.g., rotating) the handle assembly 22 in a first direction can turn the at least one light source 28 on at a first intensity. After releasing the handle assembly 22, the handle assembly 22 will return to an initial position. The handle assembly 22 can then be moved (e.g., rotated) again in the first direction a plurality of times, with each movement (e.g., rotation) increasing the intensity of the at least one light source 28. The handle assembly 22 can be moved (e.g., rotated) in a second direction opposite to the first direction to decrease the intensity of the at least one light source 28, with each successive movement (e.g., rotation) decreasing the intensity of the at least one light source 28 until the at least one light source 28 is at its lowest intensity. It is contemplated that the at least one light source 28 could be turned off by turning the handle assembly 22 in the second direction and holding the handle assembly 22 in a furthest moved (e.g., rotational) position for a set period of time. The method of altering the intensity of light of the at least one light source 28 can be done using any of the methods 200, 206 and 212 for altering a characteristic of the light assembly 12 as outlined above. Altering an intensity of a light source 28 is well known to those skilled in the art.

Another characteristic of the light assembly 12 that can be altered is a focus area or spot size of the light emitted from the at least one light source 28. A focus area or spot size could be adjusted by activating or deactivating some, but not all, of the light sources 28 (e.g., activating or deactivating the LEDs that illuminate an outer perimeter of a spot when all LEDs are activated). It is also contemplated that the focus area or spot size could be altered by moving the at least one light source 28 relative to the optics 24. Altering a focus area or spot size of a light source 28 is well known to those skilled in the art. For altering the focus area or spot size, the handle assembly 22 can be moved (e.g., rotated), with every movement (e.g., rotation) in a first direction cycling through a wider focus area or spot size and every movement (e.g., rotation) in a second direction opposite to the first direction cycling through a smaller focus area or spot size. The method of altering the focus area or spot size of the light assembly 12 can be done using any of the methods 200, 206 or 212 for altering a characteristic of the light assembly 12 as outlined above.

Yet another characteristic of the light assembly 12 that can be altered is changing a color of light emitted from the light assembly 12. The color of light emitted from the light assembly 12 can be changed in any manner well known to those skilled in the art. For example, each of the at least one light sources 28 can include a plurality of LEDs that emit light at different wavelengths, such that movement (e.g., rotation) of the handle assembly 22 will illuminate only the LEDs that emit light at a first wavelength and further movement (e.g., rotation) of the handle assembly 22 will illuminate only the LEDs that emit light at a second wavelength. It is contemplated that other methods for altering the color of light emitted from the light assembly 12 can be used such as a mechanical system that places different colored filters over the at least one light source 28 during movement (e.g., rotation) of the handle assembly 22. The method of altering the color of light emitted by the light assembly 12 can be done using any of the methods 200, 206 or 212 for altering a characteristic of the light assembly 12 as outlined above.

Movement (e.g., rotation) of the handle assembly 22 using any of the methods 200, 206 and 212 for altering a characteristic of the light assembly 12 as outlined above can change any characteristic of the light assembly 12 and is not limited to the examples outlined above. Furthermore, it is contemplated that the handle assembly 22 can include any number of recessed portions and recesses, including only a single recessed portion and recess or only the inner recessed portions 112 and inner recesses 80 or only the outer recessed portions 114 and the outer recesses 82. Moreover, it is contemplated that some of the inner recessed portions 112 and inner recesses 80 can be used to alter a first characteristic and others of the inner recessed portions 112 and inner recesses 80 can be used to alter a second characteristic.

Likewise, it is contemplated that some of the outer recessed portions 114 and outer recesses 82 can be used to alter a first characteristic and others of the outer recessed portions 114 and outer recesses 82 can be used to alter a second characteristic. It is even contemplated that each individual recessed portion and associated recess can be used to alter a different characteristic of the light assembly 12. The inner recessed portions 112 and the outer recessed portions 114 can be color coded and/or have other indicia thereon or nearby to signify the characteristic of the light assembly 12 that is altered by placing a digit therein while the handle assembly 22 is moved (e.g., rotated).

Figure 8:
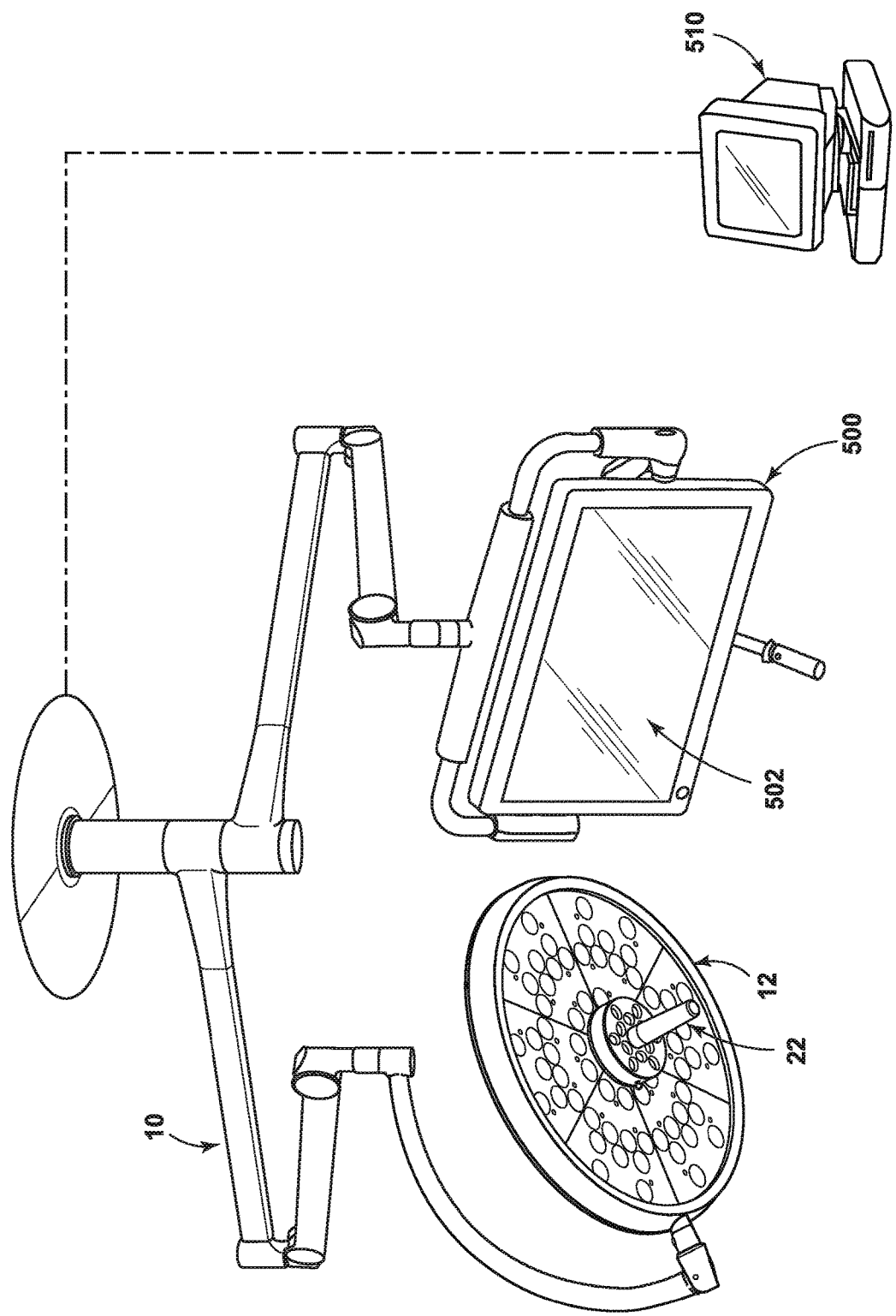
FIG. 8 is a perspective view of a comprehensive surgical light and viewing assembly according to the invention.

In the illustrated example, the handle assembly 22 can be used to alter characteristics of the light assembly 12 along with altering characteristics of other items adjacent the light assembly. FIG. 8 illustrates the surgical light 10 connected to a monitor 500 having a viewing screen 502. The viewing screen 502 of the monitor 500 can show an image or video related to a surgery taking place in an operative theater. The handle assembly 22 of the light assembly 12 can be configured to alter the image or video being shown on the viewing screen 502 of the monitor 500. For example, movement (e.g., rotation) of the handle assembly 22 according to methods 200, 206 or 212 as outlined above can change the image being shown on the viewing screen 502 or can change the source of the image or video (e.g., changing the directory of a saved video or image or changing a camera (e.g., endoscopic camera, room camera, etc.)). As illustrated in FIG. 8, the surgical light 10 can be operatively connected to a computer 510 (wired or wirelessly) to allow the characteristics that are altered by movement (e.g., rotation) of the handle assembly 22 according to methods 200, 206 or 212 to be changed. Therefore, different people using the surgical light 10 can have movement (e.g., rotation) of the handle assembly 22 perform different functions (e.g., one person can program the surgical light 10 such that movement (e.g., rotation) of the handle assembly 22 only alters characteristics of the light assembly 12 itself and another person can program the surgical light 10 such that movement (e.g., rotation) of the handle assembly 22 alters characteristics of the light assembly 12 and of the monitor 500). It is contemplated that movement (e.g., rotation) of the handle assembly 22 can alter characteristics of other devices not shown. For example, movement (e.g., rotation) of the handle assembly 22 can alter characteristics of room lights, several different monitors, an image capture and storage device, or any piece of equipment used in the same area as the surgical light 10.

In the illustrated example, the handle assembly 22 sends a first signal to a control system of the light assembly 12 when the handle assembly 22 is moved (e.g., rotated) according to method 200. The first signal can be a single analog or digital communication sent by the handle assembly 22. Alternatively, the first signal can be multiple analog or digital communications that signify that method 200 has been performed. Multiple analog or digital communications can be sent for method 200 when a first electrical communication is sent to the control system of the light assembly 12 informing the control system that the handle assembly 22 has been moved (e.g., rotated) and a second electrical communication is sent to the control system of the light assembly 12 informing the control system that no digits have been placed in any recessed portions. As illustrated in FIG. 3, the first electrical communication can be sent to the control system by the mechanism that recognizes movement (e.g., rotation) of the switch plate 292 of the handle assembly 22. The second electrical communication can be sent from the circuit board 86 through a wire 399 connected to the circuit board 86 and a first movable communication connector 396 that communicates with a second stationary communication connector (not shown) (e.g., an electrical slip ring connection). The second electrical communication can inform the control system that a digit is placed in the first recess according to method 206 or a second recess according to method 212. The second electrical communication can also inform the control system which specific recess has a digit therein for any of the methods of altering characteristics of the light assembly 12 or any other piece of equipment as outlined above. Therefore, a first signal would be that the handle assembly 22 is moved (e.g., rotated) without a digit in any recess, a second signal would be that the handle assembly 22 is moved (e.g., rotated) with a digit in a first recess, and a third signal would be that the handle assembly 22 is moved (e.g., rotated) with a digit in a third recess, with each of the first signal, second signal, and third signal being a single analog or digital communication sent by the handle assembly 22 or multiple analog or digital communications (via the switch plate 292 and the circuit board 86).

The reference numeral 22a (FIGS. 9-10) generally designates another embodiment of the present invention, having a second embodiment for the handle assembly. Since handle assembly 22a is similar to the previously described handle assembly 2, similar parts appearing in FIGS. 1-8 and FIGS. 9-10, respectively, are represented by the same, corresponding reference number, except for the suffix "a" in the numerals of the latter. Like the first embodiment of the handle assembly 22, the second embodiment of the handle assembly 22a also alters characteristics of the light assembly 12 by rotating the handle assembly 22a.

The illustrated second embodiment of the handle assembly 22a is connected to a stationary base 600 fixed to the housing 26 of the light assembly 12. The handle assembly 22a is configured to be able to rotate relative to the stationary base 600. The handle assembly 22a includes a knob 42a and a cover 44a. The knob 42a is connected to a pivot post 56a that extends through the stationary base 600 to allow the knob 42a and thereby the handle assembly 22a to rotate relative to the stationary base 600.

In the illustrated example, the stationary base 600 is fixed in position on the light assembly 12. The stationary base 600 includes an outer shell 610 having a circular top surface 602 and a peripheral skirt 604. The circular top surface 602 includes a step 606 for accommodating a portion of the cover 44a. A circuit board 608 is connected to an underside of the circular top surface 602 of the outer shell 610 of the stationary base 600. The circuit board 608 senses rotation of the handle assembly 22a. Furthermore, the circuit board 608 senses activation of an actuator 612 as discussed in more detail below. A plurality of connectors 614 connect the stationary base 600 to the housing 26 of the light assembly 12. The circular top surface 602 of the outer shell 610 of the stationary base 600 includes a central hole 616 surrounded by a connection cylinder 618 that extends upward and downward from the circular top surface 602 of the outer shell 610 of the stationary base 600. The handle assembly 22a extends through the central hole 616 and rides on a top edge 619 of the connection cylinder 618.

The illustrated handle assembly 22a is rotatably connected to the stationary base 600. The knob 42a of the handle assembly 22a includes a stepped central opening 620. The stepped central opening 620 includes a top button receiving area 622, an upper constriction area 624, a lower post receiving area 626 and a bottom cylinder receiving area 628. The bottom cylinder receiving area 628 includes a bearing step surface 630 at a top thereof defining a transition from the lower post receiving area 626 to the bottom cylinder receiving area 628. The connection cylinder 618 of the stationary base 600 is received within the bottom cylinder receiving area 628. A cupped spring washer and retaining ring 632 are located between the top edge 619 of the connection cylinder 618 and the bearing step surface 630 to allow the knob 42*a* of the handle assembly 22*a* to easily rotate on the connection cylinder 618 and to prevent movement of the pivot post 56*a* out of the knob 42*a*.

In the illustrated example, the knob 42*a* is pivotally connected to the stationary base 600. The pivot post 56*a* of the knob 42*a* is located in the lower post receiving area 626 and the bottom cylinder receiving area 628 and extends outwards from a bottom of the knob 42*a* through the central hole 616 of the circular top surface 602 of the outer shell 610 of the stationary base 600. A cotter pin 634 extends through a hole 636 in a side surface 638 of the knob 42*a* to connect the pivot post 56*a* to the knob 42*a*. A bottom surface of the pivot post 56*a* is connected to a rotation disc 336*a*. Rotation of the knob 42*a* causes rotation of the pivot post 56*a* and the rotation disc 336*a*. A ring bearing 640 surrounds a bottom of the connection cylinder 618 of the stationary base 600 and is sandwiched between the underside of the circular top surface 602 of the outer shell 610 of the stationary base 600 and the rotation disc 336*a* to maintain the rotation disc 336*a* in position and to allow for easy rotation of the rotation disc 336*a*. The rotation disc 336*a* is connected to a plurality of springs 642 to bias the rotation disc 336*a* in a central location. As is well known to those skilled in the art, the rotation disc 336*a* includes a pair of contacts that engage corresponding contacts at opposite limits of rotation of the rotation disc 336*a*. Therefore, the knob 42*a* can be rotated in a first direction to contact a first one of the contacts to close a first circuit and in a second direction to contact a second one of the contacts to close a second circuit. The springs 642 bias the rotation disc 336*a* to a location between the first one and the second one of the contacts. While a particular manner of closing two circuits is illustrated, any way of closing circuits by rotating the knob 42*a* can be employed. For example, the system disclosed in U.S. Patent Application Publication No. US2010/0053982 entitled HANDLE, the entire contents of which are hereby incorporated by reference, could be used.

The illustrated cover 44*a* covers the knob 42*a* and protects the knob 42*a*. The cover 44*a* includes a knob covering portion 100*a* and a base covering portion 102*a*. The knob covering portion 100*a* includes an outer frustoconical shell 104*a* having a slight taper and an end cap 106*a* at an end of the outer frustoconical shell 104*a*. The base covering portion 102*a* includes a disc-shaped plate 110*a* extending radially from an end of the outer frustoconical shell 104*a* opposite the end cap 106*a* and a cylindrical skirt 644 that extends from a periphery of the disc-shaped plate 110*a* toward the stationary base 600. The cylindrical skirt 644 is accommodated in step 606 of the circular top surface 602 of the outer shell 610 of the stationary base 600.

Figure 9:
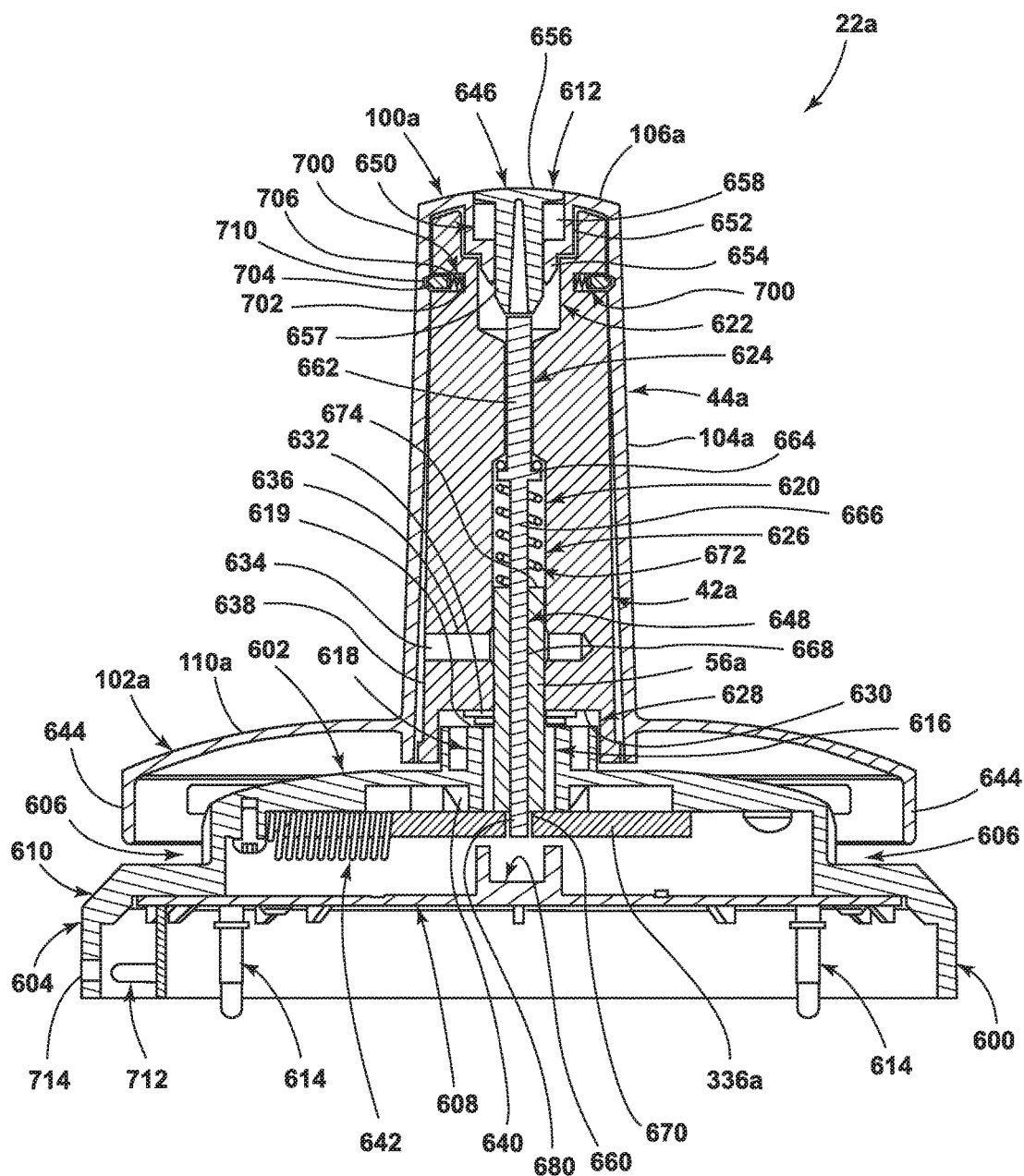
FIG. 9 is a partial cross-sectional view of a second embodiment of the handle assembly according to the invention.
Figure 10:
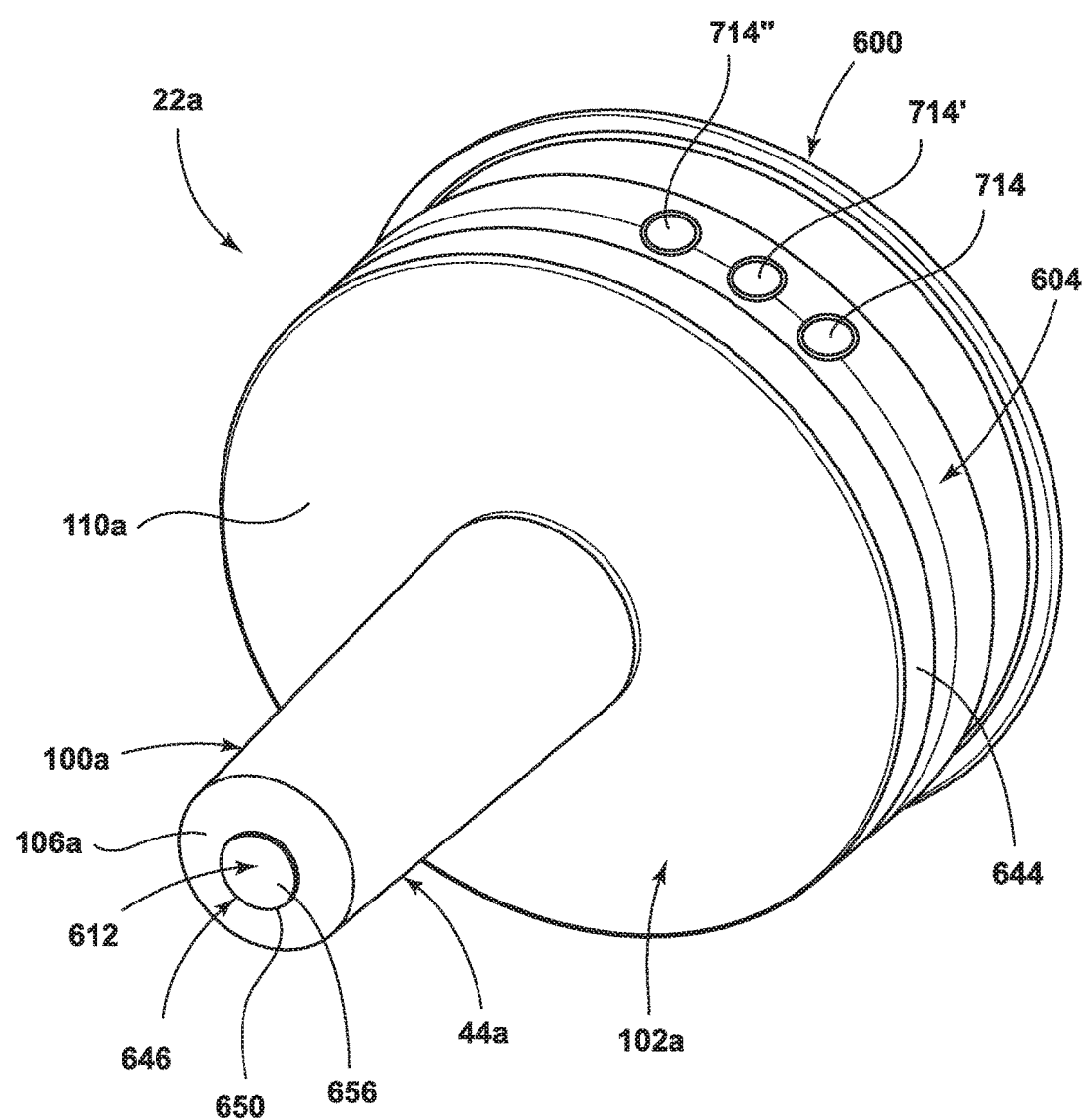
FIG. 10 is a perspective view of the second embodiment of the handle assembly according to the invention.

In the illustrated example, the actuator 612 extends from the cover 44*a* and through the knob 42*a* and is configured to be actuated to alter which characteristic of light emitted from the light assembly 12 is altered by rotating the handle assembly 22*a*. The actuator 612 includes a button 646 and a push rod 648. The button 646 is on the cover 44*a* and is configured to selectively move the push rod 648. The button 646 is located in a recess 650 in the end cap 106*a* of the knob covering portion 100*a* of the cover 44*a*. The recess 650 includes a downwardly extending cylindrical wall 652 and a plurality of guides 654 extending inwardly from a bottom surface of the cylindrical wall 652. The button 646 includes a top push surface 656 and a stem 657. The top push surface 656 is configured to be flush with the end cap 106*a* as illustrated in FIGS. 9 and 10. The stem 657 includes a plurality of vertically extending slots 658 that receive the guides 654. The guides 654 allow the button 646 to move vertically as shown in FIG. 9 by allowing the guides 654 to slide in the slots 658 of the stem 657. Depressing the top push surface 656 of the button 646 forces the push rod 648 to slide within the knob 42*a*.

The illustrated actuator 612 includes the push rod 648 that is configured to engage a sensor 660 on the circuit board 608 to alter which characteristic of light emitted from the light assembly 12 is altered by rotating the handle assembly 22*a*. The push rod 648 includes an upper portion 662 that slides within the upper constriction area 624 of the stepped central opening 620 of the knob 42*a*, a radial stop 664 at a bottom of the upper portion 662 and a lower portion 666, with the radial stop 664 defining a transition between the upper portion 662 and the lower portion 666. The radial stop 664 slides within the lower post receiving area 626 of the stepped central opening 620 of the knob 42*a*, with the radial stop 664 abutting the upper constriction area 624 for preventing the lower portion 666 of the push rod 648 from extending into the upper constriction area 624. The lower portion 666 of the push rod 648 extends through a central bore 668 in the pivot post 56*a* and a central opening 670 in the disc 336*a*. A compression spring 672 is located between the radial stop 664 and a top edge 674 of the pivot post 56*a*.

In the illustrated example, the actuator 612 is actuated to alter which characteristic of light emitted from the light assembly 12 is altered by rotating the handle assembly 22*a*. The actuator 612 is actuated by pressing down on the top push surface 656 of the button 646. As the top push surface 656 of the button 646 is depressed, the stem 657 of the button 646 is pushed downward to abut against a top of the push rod 648. The push rod 648 is then pushed downward to compress the compression spring 672 between the radial stop 664 and the top edge 674 of the pivot post 56*a*, thereby causing the push rod 648 to slide downward through the pivot post 56*a* and the disc 336*a*. At a bottom of the path of travel of the push rod 648, an actuator head 680 at a bottom of the push rod 648 actuates the sensor 660 on the circuit board 608. Once the top push surface 656 of the button 646 is released, the compression spring 672 forces the push rod 648 and thereby the button 646 upward to their home position. The actuator head 680 is smaller than the central bore 668 of the pivot post 56*a*. It is contemplated that a tension spring could be used to force the pivot post 56*a* upward by changing the location of the radial stop 664 and connecting the tension spring to the radial stop 664 and the knob 42*a* at the transition between the upper constriction area 624 and the lower post receiving area 626 of the stepped central opening 620. It is further contemplated that the actuator head 680 could abut a limit switch of the sensor 660 to actuate the switch of the sensor 660 or the sensor 660 could be a proximity sensor that senses the actuator head 680 to actuate the switch.

In the illustrated embodiment, a characteristic of light emitted from the light assembly 12 is altered by rotating the handle assembly 22*a*. As outlined above in regard to the first embodiment of the handle assembly 22, the characteristic of the light that can be altered by rotating the second embodiment of the handle assembly 22*a* includes an intensity of the light emitted from the at least one light source 28, a focus area or spot size of the light emitted from the at least one light source 28, a color of light emitted from the light assembly 12 or any other characteristic of the light assembly 12 not limited to the examples outlined above. Furthermore, it is contemplated that the handle assembly 22*a* can be used to alter characteristics of the light assembly 12 along with altering characteristics of other items adjacent the light assembly as outlined above. Each actuation of the actuator 612 will cause the system to alter a different characteristic of the light emitted from the light assembly 12 (or other item adjacent the light assembly) when the handle assembly 22*a* is rotated. For example, a first actuation of the actuator 612 can cause the intensity of the light emitted from the at least one light source 28 to change when the handle assembly 22*a* is rotated, a second actuation of the actuator 612 can cause a focus area or spot size of the light emitted from the at least one light source 28 to change when the handle assembly 22*a* is rotated, and a third actuation of the actuator 612 can cause a color of light emitted from the light assembly 12 to change when the handle assembly 22*a* is rotated. A further actuation of the actuator 612 can make the system alter the first characteristic again (to thereby allow the system to cycle through changing the different characteristics). It is contemplated that prolonged holding down of the actuator 612 or a quick series of depressions of the actuator 612 could reset the system to altering the first characteristic in the cycle. It is also contemplated that the system can reset to altering the first characteristic in the cycle after a certain time after actuation of the actuator 612 (e.g., such that the system will alter the intensity of the light when the handle is rotated if the actuator has not been actuated in a certain period of time (e.g., 10 seconds)). While a particular actuator 612 has been described, it is contemplated that other actuators could be used. For example, the sensors in the first embodiment of the handle assembly 22 could be used as an actuator to cycle through the different characteristics that are altered as the handle assembly 22 is rotated.

The illustrated handle assembly 22*a* and/or base 600 could have an auditory or visual indication of which characteristic will be altered when the handle assembly 22*a* is rotated. As illustrated in FIGS. 9 and 10, the base 600 can include a plurality of lights 712 (e.g, LEDs) that emit light though windows 714, 714', 714" in the peripheral skirt 604 of the outer shell 610 of the stationary base 600. Each light 712 can be a different color or the windows 714, 714', 714" can have lenses of different colors (e.g., red, green, yellow, etc.). Each light 900 can indicate that a different characteristic will be altered when the handle assembly 22*a* is rotated. For example, the light through the first window 714 can indicate that the intensity of the light emitted from the at least one light source 28 will change when the handle assembly 22*a* is rotated, the light through the second window 714' can indicate that the intensity of the light emitted from the at least one light source 28 will change when the handle assembly 22*a* is rotated, and the light through the third window 714" can indicate that the intensity of the light emitted from the at least one light source 28 will change when the handle assembly 22*a* is rotated. It is contemplated that voice notification, vibration notification or colored spot size outer circle could also be used to indicate which characteristic will be altered when the handle assembly 22*a* is rotated.

The illustrated cover 44*a* is configured to be locked to the knob 42*a* by a plurality of locking mechanisms 700. As shown in FIG. 9, the knob 42*a* includes a plurality of radially opening bores 702. A connection post 704 is located in each bore 702 and is biased outward outside an outer surface of the knob 42*a* by a spring 706. An inner surface of the outer frustoconical shell 104*a* of the knob covering portion 100*a* includes a channel 710 (continuous or interrupted to form a plurality of channels) configured to receive a tip of the connection post 704 therein. As the cover 44*a* is slid over the knob 42*a*, the connections posts 704 are forced into the radially opening bores 702 against the bias of the springs 706 by the inner surface of the outer frustoconical shell 104*a* of the knob covering portion 100*a* of the cover 44*a*. Once the cover 44*a* is fully inserted onto the knob 42*a*, the connection posts 704 are allowed to extend into the channel 710, thereby locking the knob 42*a* onto the cover 44*a*.

The reference numeral 22*b* (FIGS. 11-12) generally designates another embodiment of the present invention, having a third embodiment for the handle assembly. Since handle assembly 22*b* is similar to the previously described second embodiment of the handle assembly 22*a*, similar parts appearing in FIGS. 9-10 and FIGS. 11-12, respectively, are represented by the same, corresponding reference number, except for the suffix "b" in the numerals of the latter instead of an "a." Like the second embodiment of the handle assembly 22*a*, the third embodiment of the handle assembly 22*b* also alters characteristics of the light assembly 12 by rotating the handle assembly 22*b*. The third embodiment of the handle assembly 22*b* includes a different locking mechanism 716 and a hall sensor 718 sensing scheme instead of the actuator head 680 and sensor 660.

The illustrated third embodiment of the handle assembly 22*b* includes the locking mechanism 716 for locking the cover 44*b* onto the knob 42*b*. The locking mechanism 716 includes a push button 720 and a latch 722 connected to the stationary base 600*b*. The push button 720 includes a large head 724 and a shank 726. The shank 726 extends through a pair of aligned openings 728 in a pair of vertical wall portions 730 at the step 606*b* of the outer shell 610*b* of the stationary base 600*b*. A compression spring 732 is located between an inner one of the vertical wall portions 730 and a retaining ring 734 connected to the shank 726 of the push button 720. The compression spring 732 biases the push button 720 outward. The head 724 of the push button 720 can be pushed against the bias of the compression spring 732 to move the push button 720 into the stationary base 600*b*. When the head 724 of the push button 720 is pushed against the bias of the compression spring 732, the latch 722 is moved to allow the cover 44*b* to be removed from the knob 42*b*.

Figure 12:
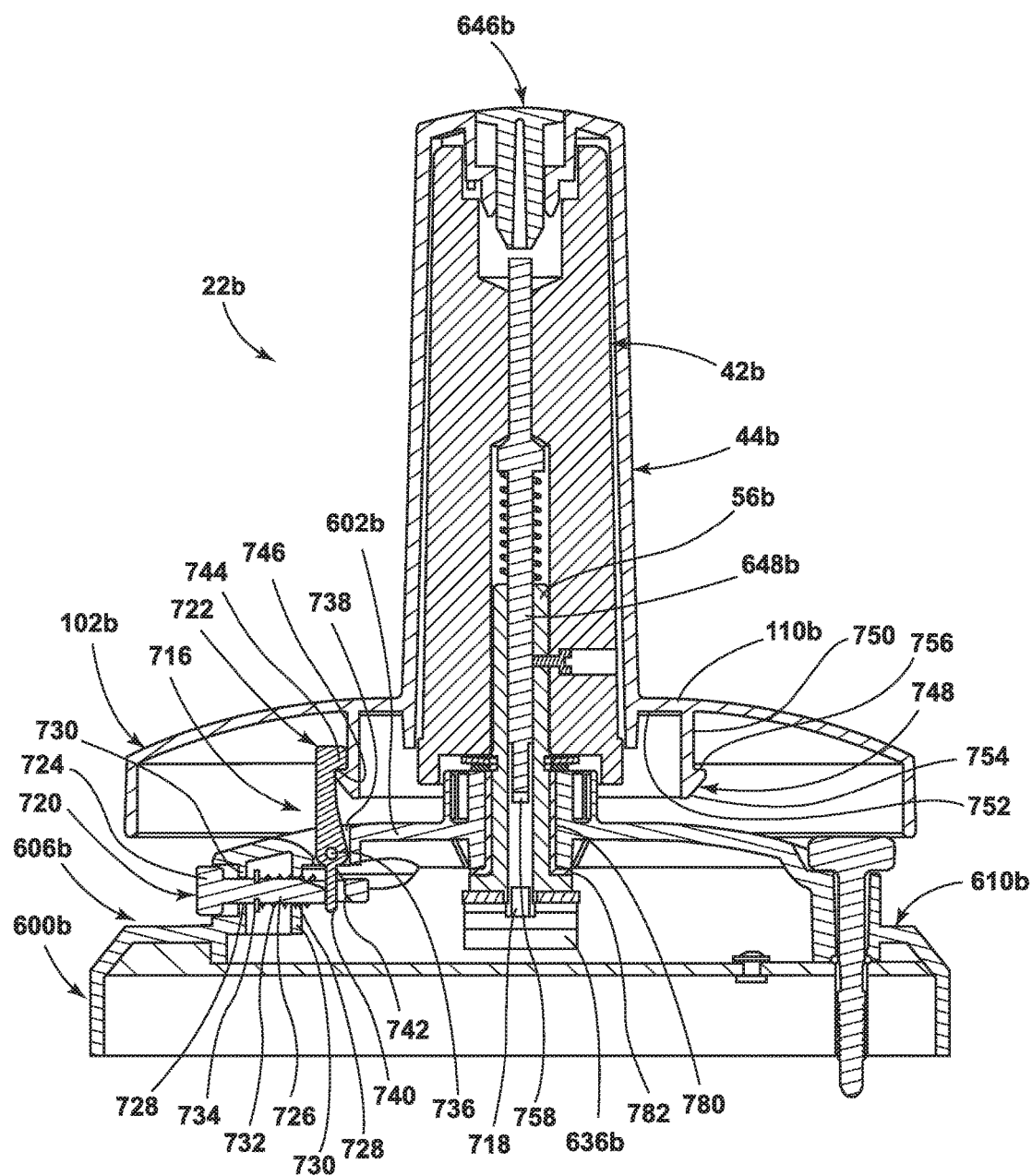
FIG. 12 is a second partial cross-sectional view of the third embodiment of the handle assembly according to the invention.

In the illustrated example, the latch 722 of the locking mechanism 716 engages with the cover 44*b* to hold the cover 44*b* on the knob 42*b*. The latch 722 is pivotally connected to the outer shell 610*b* of the stationary base 600*b* by a pivot pin 736. The latch 722 extends through an opening 738 in the circular top surface 602*b* of the outer shell 610*b*. A bottom end of the latch 722 includes a post 740 extending into a hole 742 in an end of the shank 726 of the push button 720 opposite the head 724. A top end of the latch 722 includes a lateral lip 744. As illustrated in FIG. 12, the lateral lip 744 includes a bottom edge 746 that rests on top of a holding ramp 748 at a bottom edge of an internally downwardly extending cylinder 750 extending from an inner surface 752 of the disc-shaped plate 110*b* of the base covering portion 102*b* of the cover 44*b*. The holding ramp 748 extends outwardly from a bottom of the cylinder 750 and includes a ramped bottom surface 754 and a flat top surface 756. The holding ramp 748 is located on top of the flat top surface 756 to maintain the cover 44*b* on the knob 42*b*. To remove the cover 44*b*, the large head 724 of the push button 720 is depressed, thereby moving the push button 720 against the bias of the compression spring 732 to move the hole 742 at the end of the shank 726 of the push button 720. Movement of the hole 742 causes movement of the post 740 at the bottom of the latch 722, which causes the latch 722 to pivot about the pivot pin 736, thereby removing the lateral lip 744 from engagement with the top surface of the holding ramp 748 to allow the cover 44b to be easily removed. The ramped bottom surface 754 of the holding ramp 748 allows the holding ramp 748 to automatically move the latch 722 as the cover 44b is inserted onto the knob 44b until the holding ramp 748 is below the lateral lip 744 of the latch 722, at which point the holding ramp 748 will snap back into position to hold the cover 44b on the knob 42b.

Figure 11:
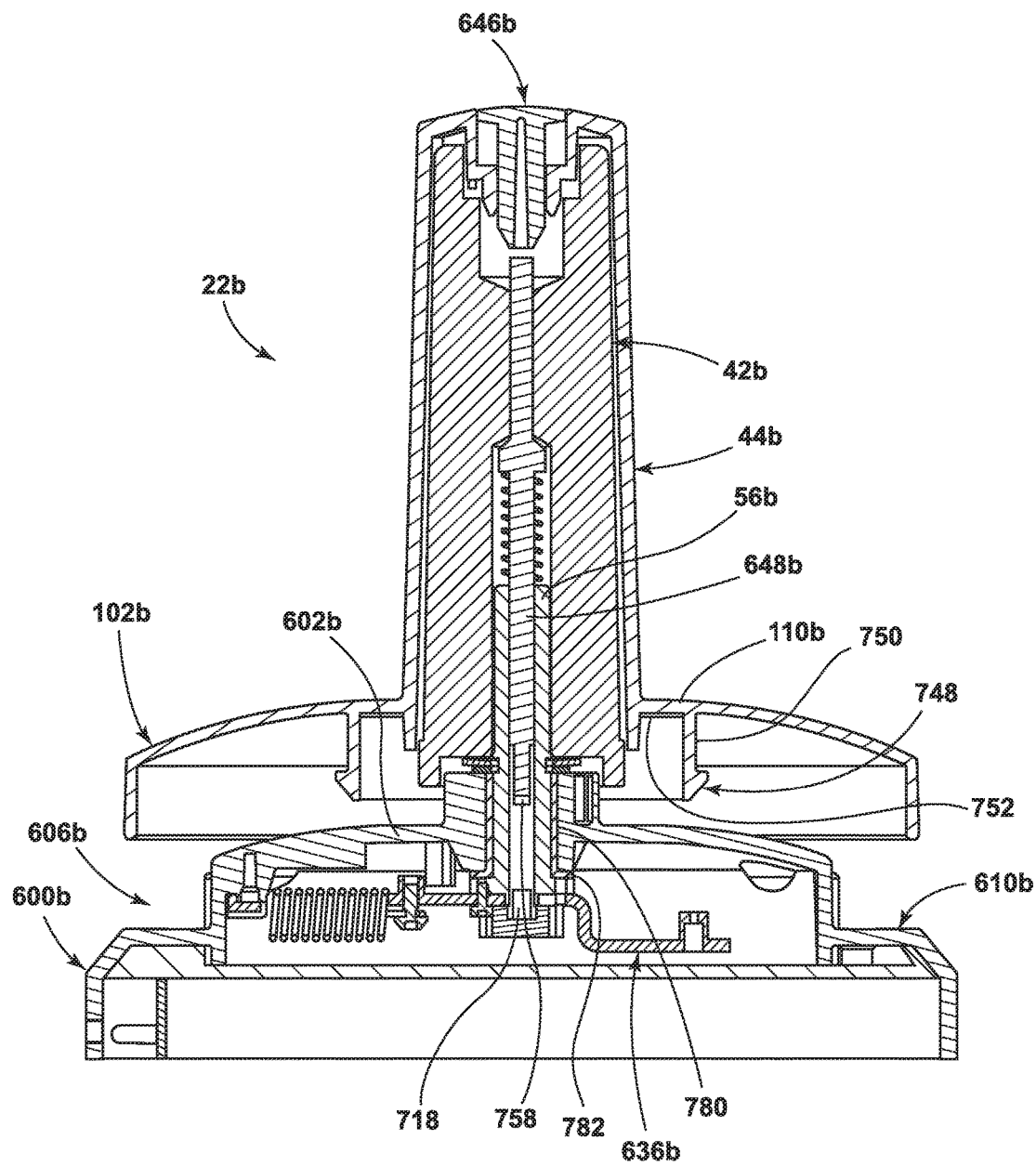
FIG. 11 is a first partial cross-sectional view of a third embodiment of the handle assembly according to the invention.

The illustrated third embodiment of the handle assembly 22b includes the hall sensor 718 for sensing actuation of the actuator 612b. As illustrated in FIGS. 11-12, a bottom of the push rod 648b includes a magnet 758. As the actuator 612b is depressed, the push rod 648b moves the magnet 758 into position adjacent the hall sensor 718 located in a middle of the rotation disc 336b, thereby allowing the hall sensor 718 to sense the magnet 758 and therefore the actuation of the actuator 612b. The hall sensor 718 then sends a signal to the control system for the handle assembly 22b that the actuator has been actuated such that a characteristic of the light assembly can be altered during rotation of the handle assembly 22b as discussed above in regard to the first embodiment of the handle assembly 22 and the second embodiment of the handle assembly 22a. As illustrated in FIGS. 11-12, a tubular bearing pad 780 having a disc-shaped bottom 782 allows the pivot post 56b and the knob 42b to easily rotate.

Although particular preferred embodiments of the invention have been disclosed in detail for illustrative purposes, it will be recognized that variations or modifications of the disclosed apparatus, including the rearrangement of parts, lie within the scope of the present invention. For example, while the drawings illustrate a handle that is rotated to alter characteristics of the light, it is contemplated that the handle could be pushed and pulled to cause axial movement of the handle to alter characteristics of the light. In this situation and when the recesses are used as in the first embodiment, it is contemplated that the light will interpret axial movement of the handle to be for positioning only when no digit is in a recess, but for altering characteristics when the axial movement is combined with digital placement in a recess.

Figure 13:
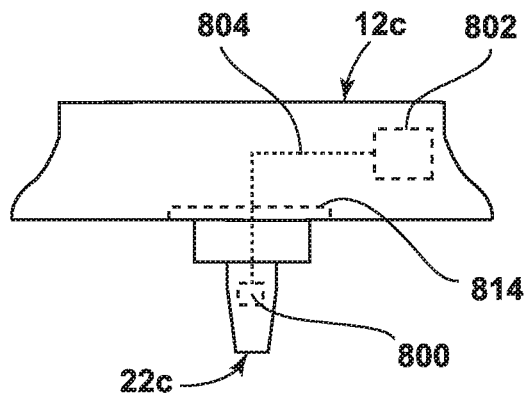
FIG. 13 is a side view of a fourth embodiment of a light assembly according to the invention.

FIG. 13 illustrates a fourth embodiment of the light assembly 12c that has a further manner of altering characteristics of light being emitted from the light assembly 12c. As illustrated in FIG. 13, the light assembly 12c includes a handle assembly 22c. However, in the fourth embodiment of the light assembly 12c, the handle assembly 22c (having a protective cover) is not rotated to alter any characteristic of light emitted from the light assembly 12c. Instead, the handle assembly 22c includes an accelerometer 800 that senses a person tapping or bumping the handle assembly 22c. Once the accelerometer 800 senses a person tapping or bumping the handle assembly 22c, the accelerometer 800 sends a signal over a communication line 804 to a control system 802 of the light assembly 12c. The control system 802 then alters the characteristic of light being emitted from the light assembly 12c or another aspect of the light assembly 12c in response to the signal.

Figure 14:
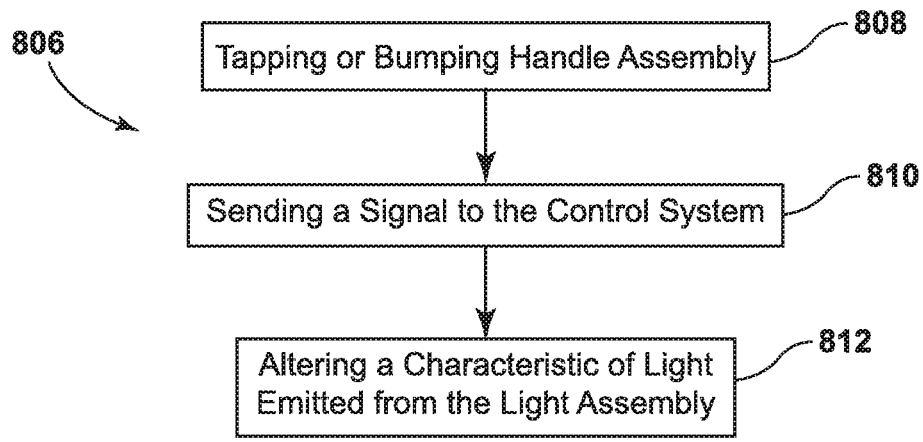
FIG. 14 illustrates a method of altering characteristics of the surgical light using the fourth embodiment of a light assembly according to the invention.

FIG. 14 illustrates a method 806 of altering a characteristic of the light assembly 12c. In a first step, the handle assembly 22c is tapped or bumped at step 808 such that the accelerometer 800 senses the tapping or bumping. It is contemplated that a dampener 814 could be located between the handle assembly 22c and the rest of the light assembly 12c to prevent the rest of the light assembly 12c from receiving the full force from the tapping or bumping of the handle assembly 22c during step 808. After the handle assembly 22c is tapped or bumped at step 808, the accelerometer 800 sends a signal over the communication line 804 to the control system 802 at step 810. It is contemplated that the communication line 804 can be wired or wireless. Finally, at step 812, the control system 802 alters a characteristic of the light assembly 12c in response to the signal. It is contemplated that the characteristic of the light assembly 12c being altered can include altering a characteristic of the light being emitted from the light assembly 12c (e.g., altering an intensity of the light emitted from the at least one light source 28 in the light assembly 12c, altering a focus area or spot size of the light emitted from the at least one light source 28 in the light assembly 12c, altering a color of light emitted from the light assembly 12c or altering any other characteristic of the light being emitting from the light assembly 12c). If the characteristic of the light assembly 12c that is being altered is the light being emitted from the light assembly 12c, it is contemplated that each tap or bump could cycle through options for the characteristic (e.g., increasing intensity until full intensity and then either lowering intensity or starting at the lowest intensity). It is further contemplated that a double tap or bump could be used to change the characteristic being altered with each single tap or bump. For example, each double tap could change from intensity to focus area or spot size to color of light. The characteristic could go back to the base characteristic (e.g., intensity) after a certain period of time after a double tap or bump. It is further contemplated that the characteristic of the light assembly 12c being altered could include turning on or off a camera (e.g., in the handle assembly 22 or elsewhere in a room having the light assembly 12c therein).

Figure 15:
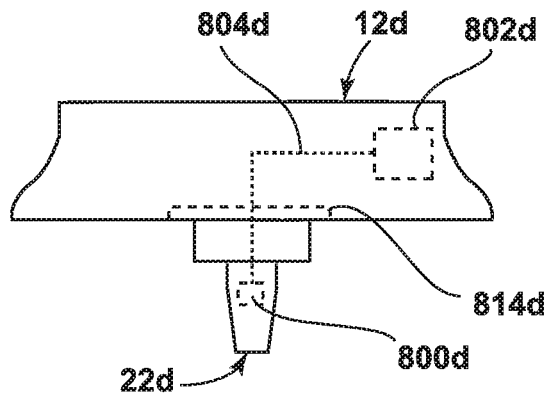
FIG. 15 is a side view of a fifth embodiment of a light assembly according to the invention.

The reference numeral 12d (FIG. 15) generally designates another embodiment of the present invention, having a fifth embodiment for the light assembly. Since light assembly 12d is similar to the previously described light assembly 12c, similar parts appearing in FIG. 13 and FIG. 15, respectively, are represented by the same, corresponding reference number, except for the suffix "d" in the numerals of the latter instead of the suffix "c" or no suffix. Like the fourth embodiment of the light assembly 12c, the fifth embodiment of the light assembly 12d includes an accelerometer 800d in the handle assembly 22d. However, in the fourth embodiment of the light assembly 12d, the handle assembly 22d is able to rotate relative to the rest of the light assembly 12d.

In the illustrated example, when the handle assembly 22d is bumped or tapped, the accelerometer 800d senses the bumping or tapping and sends a signal to the control system 802d over the communication line 804d. It is contemplated that the light assembly 12d could include a dampener 814d to prevent the rest of the light assembly 12d from receiving the full force from the tapping or bumping of the handle assembly 22d during tapping or bumping thereof. When the handle assembly 22d of the fourth embodiment of the light assembly 12d is tapped or bumped, the control system 802d can alter a characteristic of the light assembly 12d in response to the signal as set forth in step 812 above. Alternatively, the tapping or bumping can be used to select which characteristic of the light assembly 12d is altered while the handle assembly 22d is rotated. As outlined above in regard to the first embodiment of the handle assembly 22, the characteristic of the light assembly 12d that can be altered by rotating the handle assembly 22d includes altering an intensity of the light emitted from the at least one light source 28, altering a focus area or spot size of the light emitted from the at least one light source 28, altering a color of light emitted from the light assembly 12d or altering any other characteristic of the light assembly 12d not limited to the examples outlined above. Furthermore, it is contemplated that the handle assembly 22d can be used to alter characteristics of the light assembly 12d along with altering characteristics of other items adjacent the light assembly 12d as outlined above. Each bump or tap of the handle assembly 22d will cause the control system 802d to alter a different characteristic of the light emitted from the light assembly 12d (or other item adjacent the light assembly 12d) when the handle assembly 22d is rotated. For example, a bump or tap can cause the intensity of the light emitted from the at least one light source 28 to change when the handle assembly 22d is rotated, a second bump or tap can cause a focus area or spot size of the light emitted from the at least one light source 28 to change when the handle assembly 22d is rotated, and a third bump or tap can cause a color of light emitted from the light assembly 12d to change when the handle assembly 22d is rotated. A further bump or tap can make the system alter the first characteristic again (to thereby allow the system to cycle through changing the different characteristics). It is also contemplated that the system can reset to altering the first characteristic in the cycle after a certain time after bumping or tapping.

Figure 16:
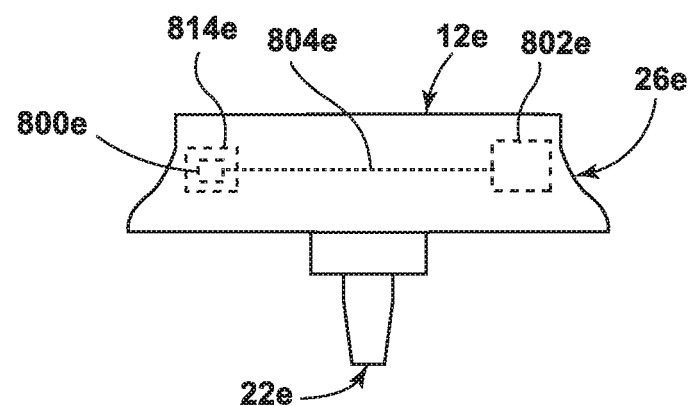
FIG. 16 is a side view of a sixth embodiment of a light assembly according to the invention.

The reference numeral 12e (FIG. 16) generally designates another embodiment of the present invention, having a sixth embodiment for the light assembly. Since light assembly 12e is similar to the previously described light assembly 12c, similar parts appearing in FIG. 13 and FIG. 16, respectively, are represented by the same, corresponding reference number, except for the suffix "e" in the numerals of the latter instead of the suffix "c" or no suffix. Like the fourth embodiment of the light assembly 12c, the sixth embodiment of the light assembly 12e includes an accelerometer 800e. However, in the sixth embodiment of the light assembly 12e, the accelerometer 800e is located in the housing 26e of the light assembly 12e instead of in the handle assembly 22e. It is contemplated that the accelerometer 800e located in the housing 26e could be isolated by a dampener 814e. Therefore, when the housing 26e is tapped or bumped, the accelerometer 800e sends a signal over the communication line 804e to the control system 802e and the control system 802e alters a characteristic of the light assembly 12e in response to the signal.

Figure 17:
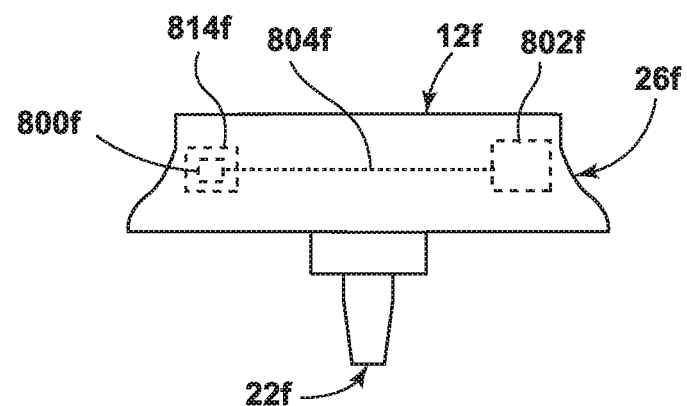
FIG. 17 is a side view of a seventh embodiment of a light assembly according to the invention.

The reference numeral 12f (FIG. 17) generally designates another embodiment of the present invention, having a seventh embodiment for the light assembly. Since light assembly 12f is similar to the previously described light assembly 12d, similar parts appearing in FIG. 15 and FIG. 17, respectively, are represented by the same, corresponding reference number, except for the suffix "f" in the numerals of the latter instead of the suffix "d." Like the fifth embodiment of the light assembly 12d, the seventh embodiment of the light assembly 12f includes an accelerometer 800f. However, in the seventh embodiment of the light assembly 12f, the accelerometer 800f is located in the housing 26f of the light assembly 12f instead of in the handle assembly 22f. It is contemplated that the accelerometer 800f located in the housing 26l could be isolated by a dampener 814f. Therefore, when the housing 26l is tapped or bumped, the accelerometer 800l sends a signal over the communication line 804f to the control system 802f and the control system 802f alters a characteristic of the light assembly 12f in response to the signal (either automatically or when the handle assembly 22l is rotated as outlined above).

According to the fourth through seventh embodiments of the light assembly 12c-12f, a surgical light is provided. The surgical light includes a light housing having at least one light source therein, a handle assembly extending from the light housing and a motion sensing device for sensing quick, small movement of the motion sensing device. Bumping or tapping the surgical light at the motion sensing device causes alteration of a characteristic of light emitted from the at least one light source. The motion sensing device can be an accelerometer located in the light housing or the handle assembly.

Figure 18:
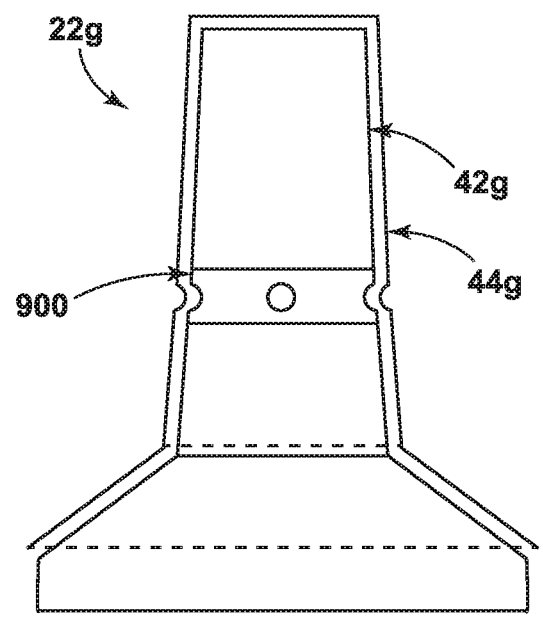
FIG. 18 is a side view of an eighth embodiment of the handle assembly according to the invention.

The reference numeral 22g (FIGS. 18-20) generally designates another embodiment of the present invention, having an eighth embodiment for the handle assembly. Since handle assembly 22g is similar to the previously described handle assembly 22, similar parts appearing in FIG. 1 and FIGS. 18-20, respectively, are represented by the same, corresponding reference number, except for the suffix "g" in the numerals of the latter. The eighth embodiment of the handle assembly 22g includes a knob 42g and a cover 44g covering the knob 42g. The knob 42g is configured to be rotated to alter one of the characteristics of the light assembly as outlined above. The knob 42g also includes a multiaxis controller 900 for either altering another characteristic of the light assembly as outlined above (i.e., different than the characteristic altered by rotation of the knob 42g) or for controlling which characteristic is altered by rotation of the knob 42g. While the multiaxis controller 900 is illustrated as rotating with the rest of the knob 42g, it is contemplated that the multiaxis controller 900 could be separate from the knob 42g such that the multiaxis controller 900 does not rotate with rotation of the knob 42g (e.g., when the multiaxis controller 900 is at a base of the handle assembly 22g).

In the illustrated example, the knob 42g has the multiaxis controller 900 located therein. The knob 42g of the eighth embodiment of the handle assembly 22g includes an upper knob portion 902 and a lower knob portion 904 (see FIG. 19). The upper knob portion 902 is connected to the lower knob portion 904 by a plurality of posts 906 (see FIGS. 19 and 20). It is contemplated that the posts 906 can be slidably received within at least one of the upper knob portion 902 and the lower knob portion 904 to allow the upper knob portion 902 to be connected to the lower knob portion 904 and to thereby capture the multiaxis controller 900 between the upper knob portion 902 and the lower knob portion 904.

The illustrated multiaxis controller 900 is configured to move along an axis of the knob 42g. The multiaxis controller 900 (FIGS. 18-20) includes an outer ring 910 and a plurality of spanning rods 912 extending radially from a center of the multiaxis controller 900 and connected to an inner cylindrical surface 914 of the outer ring 910. In the illustrated embodiment, the multiaxis controller 900 defines a post receiving area 916 between each pair of adjacent spanning rods 912 having an outer boundary defined by the inner cylindrical surface 914 of the outer ring 910. The illustrated embodiment includes one of the posts 906 of the knob 42g in each of the post receiving areas 916. While four posts 906 and four post receiving areas 916 are shown, it is contemplated that any number of posts 906 and post receiving areas 916 could be used.

Figure 19:
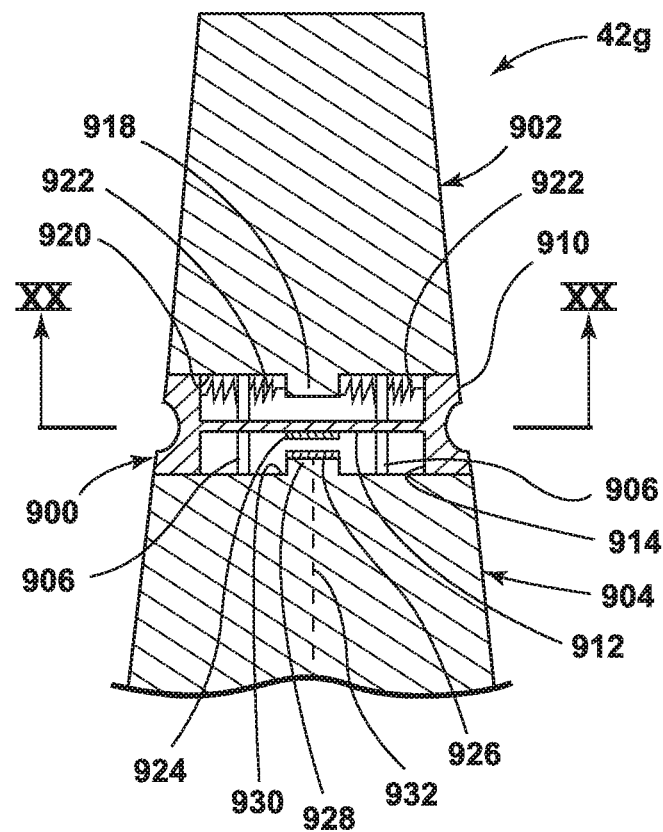
FIG. 19 is a cross-sectional view of a portion of the eighth embodiment of the handle assembly according to the invention.
Figure 20:
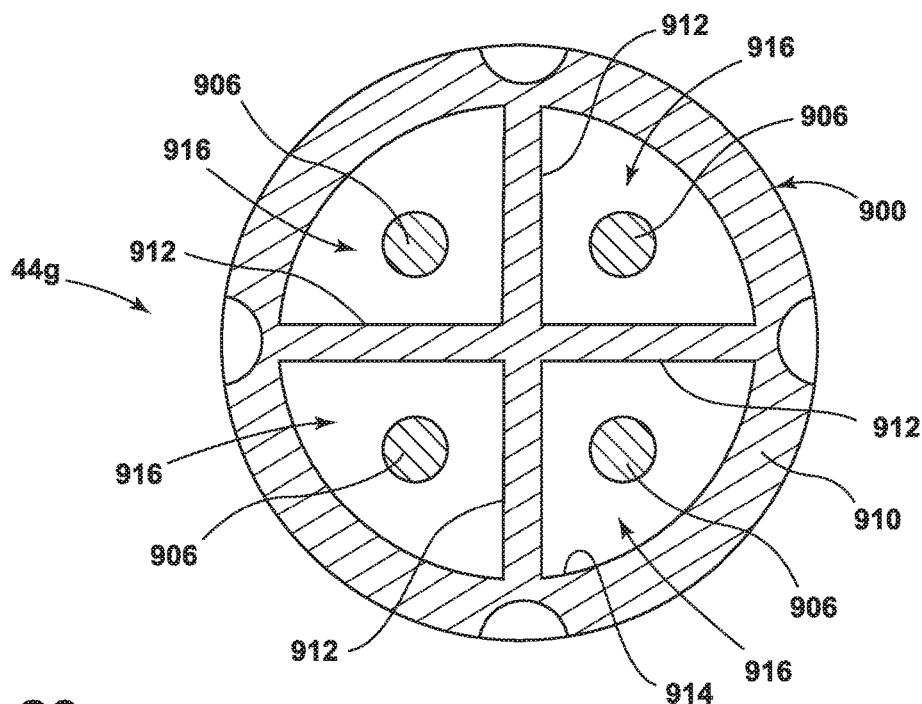
FIG. 20 is a cross-sectional view of a portion of the eighth embodiment of the handle assembly according to the invention taken along line XX-XX of FIG. 19.

As illustrated in FIG. 19, the upper knob portion 902 of the knob 42g includes a central tab 918 extending downwardly toward the lower knob portion 904 from a bottom surface 920 of the upper knob portion 902. The central tab 918 includes a plurality of springs 922 connected to a peripheral surface thereof and connected to the inner cylindrical surface 914 of the outer ring 910. The springs 922 are preferably equally spaced on the peripheral surface of the central tab 918 and the inner cylindrical surface 914 of the outer ring 910 to maintain the multiaxis controller 900 in a central or home location. In the illustrated embodiment, the central or home location is centrally located along an axis of rotation of the knob 42g.

In the illustrated embodiment, the multiaxis controller 900 is moved off of the axis of rotation of the knob 42g to alter a characteristic of the light assembly or for controlling which characteristic is altered by rotation of the knob 42g. As illustrated in FIG. 19, the multiaxis controller 900 can include a sensed object 924 (e.g., a magnet) located in a center thereof. As shown in FIG. 19, the sensed object 924 is connected to a bottom of an intersection of the spanning rods 912 of the multiaxis controller 900. The lower knob portion 904 of the knob 42g includes a sensor 926 (e.g., a magnetometer or hall sensor) on a platform 928 in a central location of a top surface 930 of the lower knob portion 904. The sensor 926 senses when the sensed object 924 has moved off center when the multiaxis controller 900 is moved away from the central or home location.

The illustrated multiaxis controller 900 can be moved laterally off of the axis of rotation of the knob 42g to actuate the multiaxis controller 900. When a person grasps the knob 42g, the person can selectively push the multiaxis controller 900 laterally against the bias of the spring 922. The cover 44g is pliable enough to allow for the multiaxis controller 900 to be moved laterally. Once the multiaxis controller 900 is moved off the central or home location, the sensor 926 will sense that the sensed object 924 has moved. The sensor 926 will then send a signal over a communication line 932 to a control system of the light assembly. It is contemplated that the communication line 932 can be wired or wireless. The signal makes the control system alter a characteristic of the light assembly in response to the signal. It is contemplated that the characteristic of the light assembly being altered can include altering a characteristic of the light being emitted from the light assembly (e.g., altering an intensity of the light emitted from the at least one light source 28 in the light assembly, altering a focus area or spot size of the light emitted from the at least one light source 28 in the light assembly, altering a color of light emitted from the light assembly or altering any other characteristic of the light being emitting from the light assembly). If the characteristic of the light assembly that is being altered is the light being emitted from the light assembly, it is contemplated that each movement of the multiaxis controller 900 could cycle through options for the characteristic (e.g., increasing intensity until full intensity and then either lowering intensity or starting at the lowest intensity). It is further contemplated that a double movement could be used to change the characteristic being altered with each single movement. For example, each double movement could change from intensity to focus area or spot size to color of light. The characteristic could go back to the base characteristic (e.g., intensity) after a certain period of time after a double movement. It is further contemplated that the characteristic of the light assembly being altered could include turning on or off a camera (e.g., in the handle assembly or elsewhere in a room having the light assembly therein). Alternatively, each movement of the multiaxis controller 900 could cause the control system to alter a different characteristic of the light emitted from the light assembly (or other item adjacent the light assembly) when the handle assembly 22g is rotated. For example, a first movement of the multiaxis controller 900 can cause the intensity of the light emitted from the at least one light source 28 to change when the handle assembly 22g is rotated, a second movement of the multiaxis controller 900 can cause a focus area or spot size of the light emitted from the at least one light source 28 to change when the handle assembly 22g is rotated, and a third movement of the multiaxis controller 900 can cause a color of light emitted from the light assembly to change when the handle assembly 22g is rotated. A further movement of the multiaxis controller 900 can make the system alter the first characteristic again (to thereby allow the system to cycle through changing the different characteristics). It is also contemplated that the system can reset to altering the first characteristic in the cycle after a certain time after movement of the multiaxis controller 900.

The reference numeral 44h (FIG. 21) generally designates another embodiment of the present invention, having a ninth embodiment of a knob for the handle assembly. Since knob 44h is similar to the previously described knob 44g, similar parts appearing in FIG. 20 and FIG. 21, respectively, are represented by the same, corresponding reference number, except for the suffix "h" in the numerals of the latter instead of the suffix "g" or non-suffix. The ninth embodiment of the knob 44h does not include the sensor 926 or the sensed object 924 for sensing any movement of the multiaxis controller 900h. Instead, the multiaxis controller 900h of the ninth embodiment of the knob 44h includes sensors for sensing multiple directions of movement of the multiaxis controller 900h.

In the illustrated example, the multiaxis controller 900h includes an outer ring 910h and four spanning rods 912h defining four post receiving areas 916h for receiving posts 906h. A first pair of opposite posts 906h includes a pair of first sensors 933, 933' (e.g., a magnetometer, hall sensor or first contact) facing an inner cylindrical surface 914h of the outer ring 910h. The outer ring 910h includes a pair of complementary first sensed objects 931, 931' (e.g., magnets or second contacts) facing the first sensors 933, 933'. When the multiaxis controller 900h is moved such that one of the first sensed objects 931, 931' comes close to or in contact with the first sensors 933, 933', a signal is sent to the control system to alter a characteristic of the light assembly.

Figure 21:
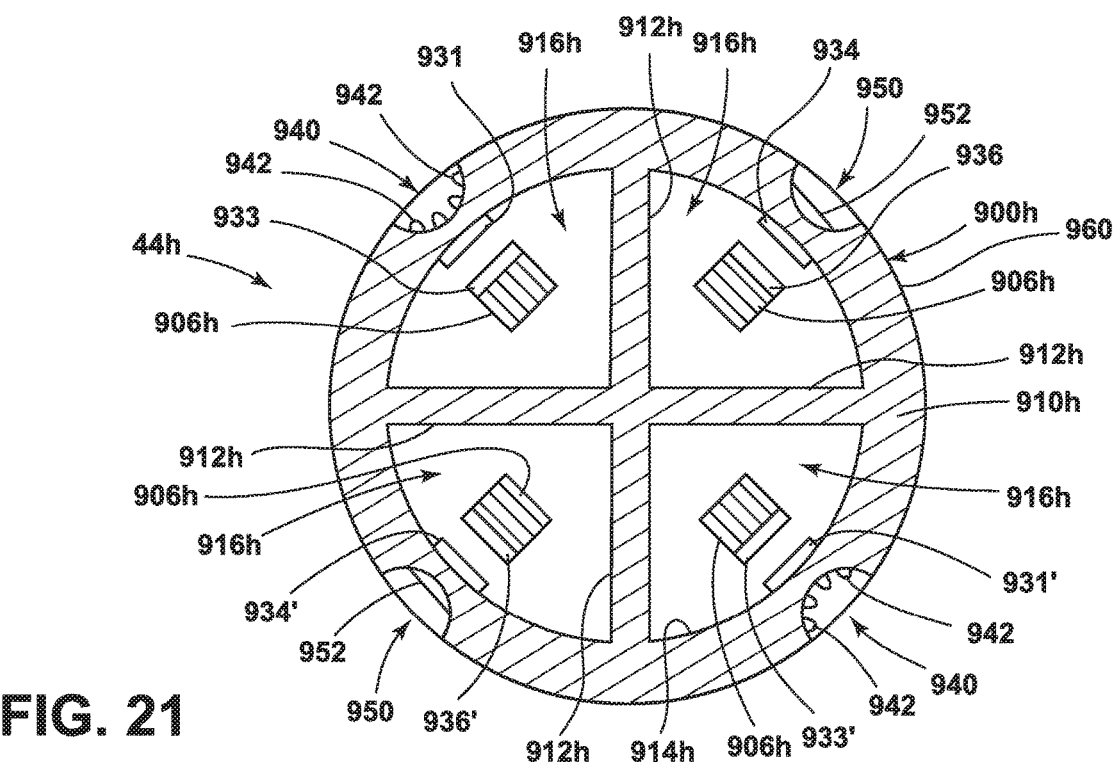
FIG. 21 is a cross-sectional view of a portion of a ninth embodiment of the handle assembly according to the invention.

It is contemplated that when the illustrated multiaxis controller 900h is moved such that the first sensed object 931 comes close to or in contact with the first sensor 933 that the characteristic is altered in one direction, while moving the multiaxis controller 900h such that the first sensed object 931' comes close to or in contact with the first sensor 933' causes the characteristic to be altered in an opposite direction. For example, it is contemplated that moving the multiaxis controller 900h such that the first sensed object 931 comes close to or in contact with the first sensor 933 will increase the intensity of light emitted from the light assembly and that moving the multiaxis controller 900h such that the first sensed object 931' comes close to or in contact with the first sensor 933' will decrease the intensity of light emitted from the light assembly. As illustrated in FIG. 21, first finger recesses 940 can be located in an outer face 960 of the outer ring 910h opposite the first sensed objects 931, 931' to assist in aligning the movement of the multiaxis controller 900h such that the first sensed objects 931, 931' come close to or in contact with the first sensors 933, 933'. Furthermore, it is contemplated that the first finger recesses 940 can include a tactile element 942 (e.g., vertical ridges) or that a tactile element could be used instead of the first finger recesses 940 for allowing a user of the light assembly to know which characteristic of the light assembly is being altered without looking at the multiaxis controller 900h.

In the illustrated example, a second pair of opposite posts 906h includes a pair of second sensors 936, 936' (e.g., a magnetometer, hall sensor or first contact) facing an inner cylindrical surface 914h of the outer ring 910h. The outer ring 910h includes a pair of complementary second sensed objects 934, 934' (e.g., magnets or second contacts) facing the second sensors 936, 936'. When the multiaxis controller 900h is moved such that one of the second sensed objects 934, 934' comes close to or in contact with the second sensors 936, 936', a signal is sent to the control system to alter a characteristic of the light assembly. Like the first sensed object 931, 931' and the first sensors 933, 933', the second sensed object 934, 934' and the second sensors 936, 936' can alter a characteristic an opposite direction. For example, it is contemplated that moving the multiaxis controller 900h such that the second sensed object 934 comes close to or in contact with the second sensor 936 will increase a spot size of light emitted from the light assembly and that moving the multiaxis controller 900h such that the second sensed object 934' comes close to or in contact with the second sensor 936' will decrease the spot size of light emitted from the light assembly. As illustrated in FIG. 21, second finger recesses 950 can be located in the outer face 960 of the outer ring 910h opposite the second sensed objects 934, 934' to assist in aligning the movement of the multiaxis controller 900h such that the second sensed objects 934, 934' come close to or in contact with the second sensors 936, 936'. Furthermore, it is contemplated that the second finger recesses 950 can include a tactile element 952 (e.g., horizontal ridges) or that a tactile element could be used instead of the second finger recesses 950 for allowing a user of the light assembly to know which characteristic of the light assembly is being altered without looking at the multiaxis controller 900h.

In the illustrated example, the first characteristic altered by engagement of the first sensed object 931, 931' and the first sensors 933, 933' is different than the second characteristic altered by engagement of the second sensed object 934, 934' and the second sensors 936, 936'. However, it is contemplated that the first and second sensors can alter the same characteristic when the first and second sensed objects are sensed. Furthermore, instead of the sensor and sensed objects, it is contemplated that other manners of sensing movement of the multiaxis controller could be used. For example, strain gauges could be used to determine the direction and magnitude of movement of the multiaxis controller (with magnitude possibly being used to determine the amount that the characteristic of the light assembly is altered).

Figure 22:
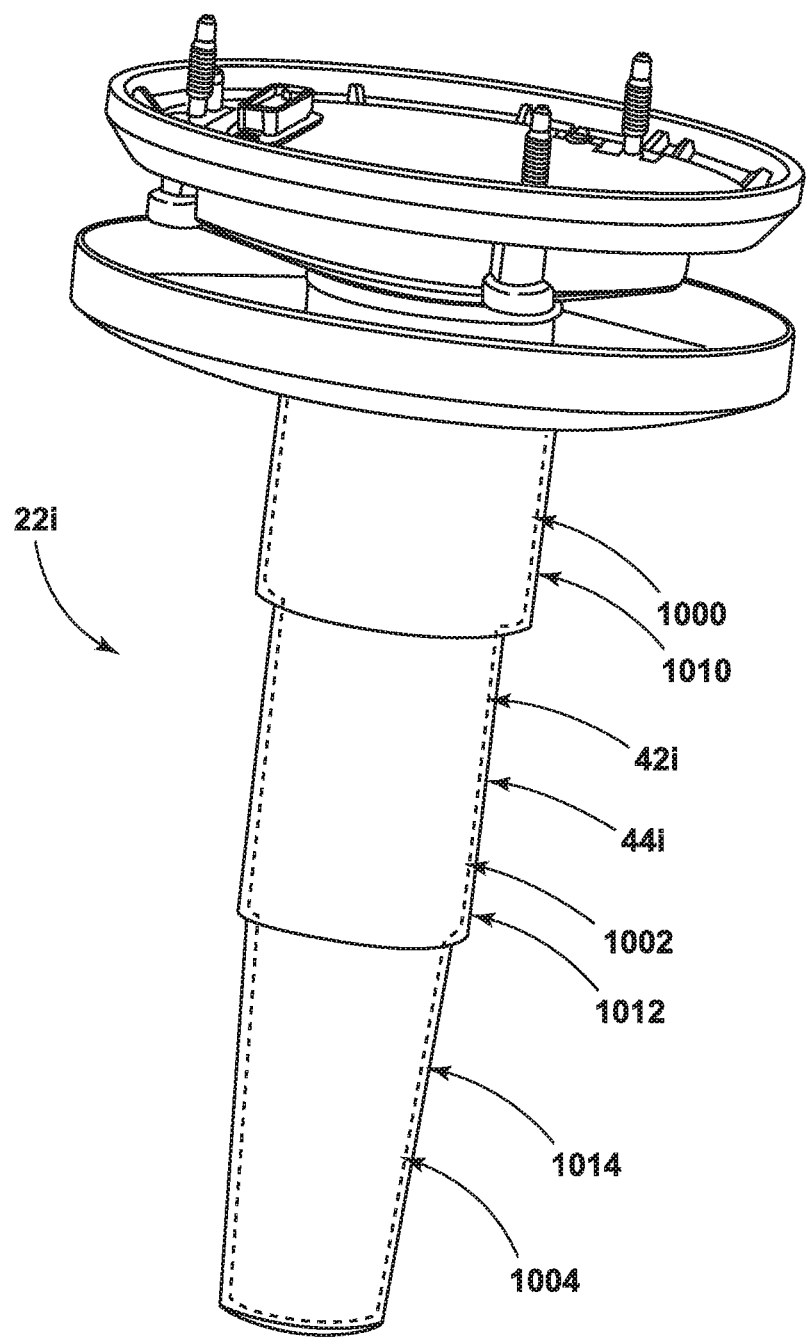
FIG. 22 is a perspective view of a tenth embodiment of the handle assembly according to the invention.

The reference numeral 22i (FIG. 22) generally designates another embodiment of the present invention, having a tenth embodiment for the handle assembly. Since handle assembly 22i is similar to the previously described handle assembly 22, similar parts appearing in FIGS. 1-8 and FIG. 22, respectively, are represented by the same, corresponding reference number, except for the suffix "i" in the numerals of the latter. Like the first embodiment of the handle assembly 22, the tenth embodiment of the handle assembly 22i also alters characteristics of the light assembly 12 by rotating the handle assembly 22i. Instead of having recesses 80, 82 and corresponding recessed portions 112, 114 adjacent proximity sensors 90 as in the first embodiment of the handle assembly 22, the tenth embodiment of the handle assembly 22i includes a multilevel knob 42i and a multilevel cover 44i.

In the illustrated example, the multilevel knob 421 includes a proximal level 1000 having a largest outer diameter, a middle level 1002 having a middle outer diameter and a distal level 1004 having a smallest outer diameter. The cover 44i includes a corresponding proximal cover level 1010, a middle cover level 1012 and a distal cover level 1014 covering the proximal level 1000, the middle level 1002 and the distal level 1004 of the knob 42i, respectively. The proximal level 1000, the middle level 1002 and the distal level 1004 of the knob 42i each include a separate sensor (e.g., a capacitance touch sensor or proximity sensor) that senses when a particular level is grasped. It is contemplated that the multilevel knob 42i and cover 44i could have only two levels or more than three levels.

The illustrated multilevel knob 42i is grasped through the cover 44i in multiple manners to alter the characteristics of the light assembly when the handle assembly 22i is rotated. As outlined above in regard to the first embodiment of the handle assembly 22, the characteristic of the light that can be altered by rotating the tenth embodiment of the handle assembly 22i includes an intensity of the light emitted from the at least one light source, a focus area or spot size of the light emitted from the at least one light source, a color of light emitted from the light assembly or any other characteristic of the light assembly not limited to the examples outlined above. Furthermore, it is contemplated that the handle assembly 22i can be used to alter characteristics of the light assembly along with altering characteristics of other items adjacent the light assembly as outlined above.

In the illustrated example, the multilevel knob 42i is grasped in a first manner by grasping one of the levels or selected adjacent levels to alter which characteristic of light emitted from the light assembly 12 is altered by rotating the handle assembly 22. Each manner of grasping of the actuator 612 will cause the system to alter a different characteristic of the light emitted from the light assembly 12 (or other item adjacent the light assembly) when the handle assembly 22i is rotated. For example, grasping only the distal level 1004, the proximal level 1000 and the middle level 1002 can cause the intensity of the light emitted from the at least one light source to change when the handle assembly 22i is rotated, grasping the middle level 1002 and the distal level 1004 can cause a focus area or spot size of the light emitted from the at least one light source to change when the handle assembly 22i is rotated, and grasping the proximal level 1000 and the middle level 1002 can cause a color of light emitted from the light assembly to change when the handle assembly 22i is rotated. While a particular grasping scheme has been described, it is contemplated that other grasping schemes could be used. For example, the proximal level 1000, the middle level 1002 and the distal level 1004 could all be grasped to change the color of light. It is contemplated that the control system can be located in the handle assembly 22i or anywhere else in the light assembly. Furthermore, instead of different diameters, it is contemplated that the multilevel cover 44i and/or knob 42i could include different textures or different shapes (e.g., circular, square, oval, etc.) to differentiate the different areas that are grasped to alter different characteristics of light emitted from the light assembly. It is further contemplated that an actuator as discussed above could be included in the handle assembly 22i for altering different characteristics of light or for turning on and off the grasping features for altering different characteristics of light in the tenth embodiment of the handle assembly 22i.

Although particular preferred embodiments of the invention have been disclosed in detail for illustrative purposes, it will be recognized that variations or modifications of the disclosed apparatus, including the rearrangement of parts or modifying state-machine (logic sequence) of software, lie within the scope of the present invention. For example, for any of the embodiment outlined above, it is contemplated that the handle must be turned and held for a particular period of time before the characteristic of light emitted from the light assembly will alter.

What is claimed is:

1. A surgical light comprising:
a light housing having at least one light source therein; and
a handle assembly extending from the light housing, the handle assembly including a base, a knob and a cover;
the base having at least one first sensor at a face of the base;
the knob extending from the face of the base and being connected to the base;
the cover covering the knob and the face of the base, the cover including at least one first area for covering the at least one first sensor;
the knob and the cover being movably mounted relative to the light housing;
movement of the knob and the cover without engagement of the at least one first sensor by placing a digit of a user at the at least one first area causes alteration of a first characteristic of light emitted from the at least one light source; and
movement of the knob and the cover with engagement of the at least one first sensor by placing the digit of the user at the at least one first area causes alteration of a second characteristic of light emitted from the at least one light source.

2. The surgical light according to claim 1, wherein:
the base further has at least one second sensor at the face of the base;
the cover further includes at least one second area for covering the at least one second sensor; and
movement of the knob and the cover with engagement of the at least one second sensor by placing the digit of the user at the at least one second area causes alteration of a third characteristic of light emitted from the at least one light source.

3. The surgical light according to claim 1, wherein:
the at least one first sensor is a proximity sensor sensing placement of the digit into the at least one first area.

4. The surgical light according to claim 1, wherein:
the face comprises a recess covering the at least one first sensor and the at least one first area comprises a recessed area received within the recess of the face.

5. The surgical light according to claim 1, wherein:
the cover is removably positioned on the base and the knob.

6. The surgical light according to claim 5, wherein:
the base includes a locking lever for locking the cover on the base and the knob.

7. The surgical light according to claim 1, wherein:
one of the first characteristic and the second characteristic is an intensity of the at least one light source.

8. The surgical light according to claim 1, wherein:
one of the first characteristic and the second characteristic is a size of a beam area of the at least one light source.

9. The surgical light according to claim 1, wherein:
one of the first characteristic and the second characteristic is color of light emitted from the at least one light source.

10. The surgical light according to claim 1, wherein:
the knob and the cover are rotatably mounted relative to the light housing such that rotation of the knob and the cover without engagement of the at least one first sensor by placing the digit of the user at the at least one first area causes alteration of the first characteristic of light emitted from the at least one light source and rotation of the knob and the cover with engagement of the at least one first sensor by placing the digit of the user at the at least one first area causes alteration of the second characteristic of light emitted from the at least one light source.

11. A handle assembly comprising:
a base having at least one first sensor at a face of the base;
a knob extending from the face of the base and being connected to the base;
a cover covering the knob and the face of the base, the cover including at least one first area for covering the at least one first sensor;
movement of the knob and the cover without engagement of the at least one first sensor by placing a digit of a user at the at least one first area causes the base to send a first signal; and
movement of the knob and the cover with engagement of the at least one first sensor by placing the digit of the user at the at least one first area causes the base to send a second signal.

12. The handle assembly according to claim 11, wherein:
the base further has at least one second sensor at the face of the base;
the cover further includes at least one second area for covering the at least one second sensor; and
movement of the knob and the cover with engagement of the at least one second sensor by placing the digit of the user at the at least one second area causes the base to send a third signal.

13. The handle assembly according to claim 11, wherein:
the at least one first sensor is a proximity sensor sensing placement of the digit into the at least one first area.

14. The handle assembly according to claim 11, wherein:
the face comprises a recess covering the at least one first sensor and the at least one first area comprises a recessed area received within the recess of the face.

15. The handle assembly according to claim 11, wherein:
the cover is removably positioned on the base and the knob.

16. The handle assembly according to claim 15, wherein:
the base includes a locking lever for locking the cover on the base and the knob.

17. A surgical light handle cover comprising:
a knob covering portion including a circular side wall and a top wall; and
a face plate covering portion connected to a bottom edge of the knob covering portion, the face plate covering portion including a disc-shaped plate having a top surface and a bottom surface and a plurality of recessed portions extending from the top surface of the disc-shaped plate in a direction away from the knob covering portion,
wherein the recessed portions in the disc-shaped plate include a plurality of inner recessed portions forming a first inner circle about the knob covering portion and a plurality of outer recessed portions forming a second outer circle about the inner circle of the inner recessed portions in the disc-shaped plate.

18. The surgical light handle cover of claim 17, wherein:
the circular side wall has a frustoconical shape with a slight taper.

19. The surgical light handle cover of claim 17, wherein:
the knob covering portion and the face plate covering portion are made of substantially rigid material.

20. The surgical light handle cover of claim 17, wherein:
the knob covering portion and the face plate covering portion are made of substantially flexible material.

21. A surgical light comprising:
a light housing having at least one light source therein; and
a handle assembly extending from the light housing, the handle assembly including a knob and a cover;
the knob and the cover being movably mounted relative to the light housing;
the cover covering the knob;
the handle assembly including an actuator;
a first activation of the actuator causing alteration of a first characteristic of light emitted from the at least one light source when the knob is rotated relative to the light housing; and
a second activation of the actuator causing alteration of a second characteristic of light emitted from the at least one light source when the knob is rotated relative to the light housing.

22. The surgical light according to claim 21, wherein:
a third activation of the actuator causes alteration of a third characteristic of light emitted from the at least one light source when the knob is rotated relative to the light housing.

23. The surgical light according to claim 21, wherein:
one of the first characteristic and the second characteristic is an intensity of the at least one light source.

24. The surgical light according to claim 21, wherein:
one of the first characteristic and the second characteristic is a size of a beam area of the at least one light source.

25. The surgical light according to claim 21, wherein:
one of the first characteristic and the second characteristic is color of light emitted from the at least one light source.

26. The surgical light according to claim 21, further including:
a first light for indicating that rotation of the knob will cause the first characteristic to be altered; and
a second light for indicating that rotation of the knob will cause the second characteristic to be altered.

27. The surgical light according to claim 21, wherein:
the actuator includes a button on the cover and a push rod extending through the knob; and
the button and the push rod are engaged such that movement of the button causes movement of the push rod.

28. A method of adjusting attributes of light emitted from a surgical light comprising:
providing a light housing having at least one light source therein;
providing a handle assembly extending from the light housing, the handle assembly including a knob and a cover;
rotatably connecting the handle assembly to the light housing;
covering the knob with the cover;
engaging the cover in a first mode and rotating the knob to thereby alter a first characteristic of light emitted from the at least one light source; and
engaging the cover in a second mode and rotating the knob to thereby alter a second characteristic of light emitted from the at least one light source.

29. The method of adjusting attributes of light emitted from the surgical light of claim 28, further including:
providing the handle assembly with an actuator;
wherein engaging the cover in the first mode includes actuating the actuator a first time; and
wherein engaging the cover in the second mode includes actuating the actuator a second time.

30. The method of adjusting attributes of light emitted from the surgical light of claim 28, further including:
providing the handle assembly with a base having at least one first sensor at a face of the base; and
providing the cover with at least one first area for covering the at least one first sensor;
wherein engaging the cover in the first mode includes not placing a digit of a user at the at least one first area; and
wherein engaging the cover in the second mode includes placing a digit of a user at the at least one first area.

31. The method of adjusting attributes of light emitted from the surgical light of claim 28, further including:
providing the knob with multiple levels, each of the levels having a different diameter;
wherein engaging the cover in the first mode includes grasping the knob such that at least one of the levels is not grasped; and
wherein engaging the cover in the second mode includes grasping the knob such that the at least one of the levels is grasped.

32. A surgical light comprising:
a light housing having at least one light source therein;
a handle assembly extending from the light housing, the handle assembly including a knob and a cover;
the handle assembly being rotatably connected to the light housing;
the cover covering the knob;
wherein engaging the cover in a first mode and rotating the knob alters a first characteristic of light emitted from the at least one light source; and
wherein engaging the cover in a second mode and rotating the knob alters a second characteristic of light emitted from the at least one light source.

33. The surgical light of claim 32, wherein:
the handle assembly includes an actuator;
engaging the cover in the first mode includes actuating the actuator a first time; and
engaging the cover in the second mode includes actuating the actuator a second time.

34. The surgical light of claim 32, wherein:
the handle assembly includes a base having at least one first sensor at a face of the base; and
the cover includes at least one first area for covering the at least one first sensor;
wherein engaging the cover in the first mode includes not placing a digit of a user at the at least one first area; and
wherein engaging the cover in the second mode includes placing a digit of a user at the at least one first area.

35. The surgical light of claim 32, wherein:
the knob has multiple levels, each of the levels having a different diameter;
wherein engaging the cover in the first mode includes grasping the knob such that at least one of the levels is not grasped; and
wherein engaging the cover in the second mode includes grasping the knob such that the at least one of the levels is grasped.

36. A surgical light comprising:
a light housing having at least one light source therein; and
a handle assembly extending from the light housing, the handle assembly including a knob and a cover, with the knob including a main gripping portion having an axis of rotation and a multiaxis controller having a home position with a center along the axis of rotation, the multiaxis controller being able to be moved such that the center is temporarily not at the axis of rotation;

the knob and the cover being movably mounted relative to the light housing;

the cover covering the knob;

wherein movement of the multiaxis controller such that the center is not at the axis of rotation causes alteration of a characteristic of light emitted from the at least one light source.

* * * * *